United States Patent
Frodis et al.

(10) Patent No.: US 8,382,423 B1
(45) Date of Patent: Feb. 26, 2013

(54) MICRO-SCALE AND MESO-SCALE HYDRAULICALLY OR PNEUMATICALLY POWERED DEVICES CAPABLE OF ROTATIONAL MOTION

(75) Inventors: Uri Frodis, Los Angeles, CA (US); Adam L. Cohen, Los Angeles, CA (US); Michael S. Lockard, Lake Elizabeth, CA (US)

(73) Assignee: Microfabrica Inc., Van Nuys, CA (US)

( * ) Notice: Subject to any disclaimer, the term of this patent is extended or adjusted under 35 U.S.C. 154(b) by 1174 days.

(21) Appl. No.: 12/168,787

(22) Filed: Jul. 7, 2008

Related U.S. Application Data

(63) Continuation-in-part of application No. 12/139,445, filed on Jun. 13, 2008, now Pat. No. 8,241,228, which is a continuation-in-part of application No. 10/949,744, filed on Sep. 24, 2004, now Pat. No. 7,498,714, and a continuation-in-part of application (Continued)

(51) Int. Cl.
*F04D 1/08* (2006.01)
(52) U.S. Cl. .......................... 415/83; 415/904
(58) Field of Classification Search .................. 415/904, 415/83, 84, 85, 86, 87, 903; 433/131, 132, 433/103, 120; 606/180, 170
See application file for complete search history.

(56) References Cited

U.S. PATENT DOCUMENTS

| 5,190,637 A | 3/1993 | Guckel |
| 5,718,618 A | 2/1998 | Guckel et al. |
| 6,027,630 A | 2/2000 | Cohen |
| 7,390,163 B2 * | 6/2008 | Clauson .......................... 415/83 |
| 7,611,616 B2 | 11/2009 | Cohen et al. |

OTHER PUBLICATIONS

Cohen, et al., "EFAB: Batch Production of Functional, Fully-Dense Metal Parts with Micron-Scale Features", Proc. 9th Solid Freeform Fabrication, The University of Texas at Austin, Aug. 1998, pp. 161.
Adam L. Cohen, et al., "EFAB: Rapid, Low-Cost Desktop Micromachining of High Aspect Ratio True 3-D MEMS", Proc. 12th IEEE Micro Electro Mechanical Systems Workshop, IEEE, Jan. 17-21, 1999, pp. 244-251.
F. Tseng, et al., "EFAB: High Aspect Ratio, Arbitrary 3-D Metal Microstructures Using a Low-Cost Automated Batch Process", MEMS Symposium, ASME 1999 International Mechanical Engineering Congress and Exposition, Nov. 1999.
Adam L. Cohen, "3-D Micromachining by Electrochemical Fabrication", Micromachine Devices, Mar. 1999, pp. 6-7.
Gang Zhang, et al., "EFAB: Rapid Desktop Manufacturing of True 3-D Microstructures", Proc. 2nd International Conference on Integrated MicroNanotechnology for Space Applications, The Aerospace Co., Apr. 1999.
F. Tseng, et al., "EFAB: High Aspect Ratio, Arbitrary 3-D Metal Microstructures Using a Low-Cost Automated Batch Process", 3rd International Workshop on High Aspect Ratio Microstructure Technology (HARMST'99), Jun. 1999.

(Continued)

*Primary Examiner* — Dwayne J White
(74) *Attorney, Agent, or Firm* — Dennis R. Smalley

(57) ABSTRACT

Embodiments are directed to micro-scale or meso-scale devices having hydraulic or pneumatic actuation mechanisms incorporating bearings elements (such as ball bearings, cylindrical bearings, interference bearings, or hydrostatic bearings. Devices of some embodiments are turbines. Some devices may function as medical devices. Other embodiments are directed to multi-layer, multi-material electrochemical fabrication methods for producing such devices.

14 Claims, 24 Drawing Sheets

Related U.S. Application Data

No. 12/134,188, filed on Jun. 5, 2008, now abandoned, and a continuation-in-part of application No. 12/138,404, filed on Jun. 12, 2008, now abandoned, and a continuation-in-part of application No. 12/138,395, filed on Jun. 12, 2008, now abandoned, and a continuation-in-part of application No. 11/441,578, filed on May 26, 2006, now Pat. No. 7,674,361, said application No. 12/134,188 is a continuation-in-part of application No. 11/625,807, filed on Jan. 22, 2007, now abandoned, said application No. 12/138,395 is a continuation-in-part of application No. 11/696,722, filed on Apr. 4, 2007, now abandoned, said application No. 11/625,807 is a continuation-in-part of application No. 11/598,968, filed on Nov. 14, 2006, now abandoned, and a continuation-in-part of application No. 11/582,049, filed on Oct. 16, 2006, now Pat. No. 7,686,770, and a continuation-in-part of application No. 11/478,934, filed on Jun. 29, 2006, now abandoned, and a continuation-in-part of application No. 11/444,999, filed on May 31, 2006, now abandoned, and a continuation-in-part of application No. 10/697,598, filed on Oct. 29, 2003, now abandoned, said application No. 11/696,722 is a continuation-in-part of application No. 11/582,049, filed on Oct. 16, 2006, now Pat. No. 7,686,770, said application No. 11/598,968 is a continuation-in-part of application No. 11/591,911, filed on Nov. 1, 2006, now abandoned, said application No. 11/478,934 is a continuation-in-part of application No. 10/697,597, filed on Oct. 29, 2003, now abandoned, and a continuation-in-part of application No. 10/841,100, filed on May 7, 2004, now Pat. No. 7,109,118, and a continuation-in-part of application No. 11/139,262, filed on May 26, 2005, now Pat. No. 7,501,328, and a continuation-in-part of application No. 11/029,216, filed on Jan. 3, 2005, now abandoned, said application No. 11/444,999 is a continuation-in-part of application No. 10/697,598, filed on Oct. 29, 2003, now abandoned, said application No. 11/139,262 is a continuation-in-part of application No. 10/841,383, filed on May 7, 2004, now Pat. No. 7,195,989, said application No. 11/029,216 is a continuation-in-part of application No. 10/841,300, filed on May 7, 2004, now abandoned, and a continuation-in-part of application No. 10/607,931, filed on Jun. 27, 2003, now Pat. No. 7,239,219, said application No. 10/607,931 is a continuation-in-part of application No. 10/309,521, filed on Dec. 3, 2002, now Pat. No. 7,259,640, and a continuation-in-part of application No. 10/434,497, filed on May 7, 2003, now Pat. No. 7,303,663, and a continuation-in-part of application No. 10/434,103, filed on May 7, 2003, now Pat. No. 7,160,429, and a continuation-in-part of application No. 10/434,295, filed on May 7, 2003, now abandoned, and a continuation-in-part of application No. 10/434,519, filed on May 7, 2003, now Pat. No. 7,252,861.

(60) Provisional application No. 61/018,255, filed on Dec. 31, 2007, provisional application No. 61/018,229, filed on Dec. 31, 2007, provisional application No. 60/948,262, filed on Jul. 6, 2007, provisional application No. 60/968,863, filed on Aug. 29, 2007, provisional application No. 60/943,817, filed on Jun. 13, 2007, provisional application No. 60/951,711, filed on Jul. 24, 2007, provisional application No. 60/968,042, filed on Aug. 24, 2007, provisional application No. 61/018,283, filed on Dec. 31, 2007, provisional application No. 60/506,016, filed on Sep. 24, 2003, provisional application No. 60/942,200, filed on Jun. 5, 2007, provisional application No. 60/943,310, filed on Jun. 12, 2007, provisional application No. 60/949,850, filed on Jul. 14, 2007, provisional application No. 60/951,711, filed on Jul. 24, 2007, provisional application No. 60/968,042, filed on Aug. 24, 2007, provisional application No. 61/018,283, filed on Dec. 31, 2007, provisional application No. 60/945,570, filed on Jun. 21, 2007, provisional application No. 60/951,707, filed on Jul. 24, 2007, provisional application No. 60/968,043, filed on Aug. 24, 2007, provisional application No. 61/018,303, filed on Dec. 31, 2007, provisional application No. 60/943,309, filed on Jun. 12, 2007, provisional application No. 60/968,882, filed on Aug. 29, 2007, provisional application No. 60/943,318, filed on Jun. 12, 2007, provisional application No. 60/685,130, filed on May 26, 2005, provisional application No. 60/761,401, filed on Jan. 20, 2006, provisional application No. 60/789,378, filed on Apr. 4, 2006, provisional application No. 60/726,794, filed on Oct. 14, 2005, provisional application No. 60/736,961, filed on Nov. 14, 2005, provisional application No. 60/761,401, filed on Jan. 20, 2006, provisional application No. 60/695,328, filed on Jun. 29, 2005, provisional application No. 60/686,496, filed on May 31, 2005, provisional application No. 60/422,007, filed on Oct. 29, 2002, provisional application No. 60/732,413, filed on Nov. 1, 2005, provisional application No. 60/736,961, filed on Nov. 14, 2006, provisional application No. 60/761,401, filed on Jan. 20, 2006, provisional application No. 60/422,008, filed on Oct. 29, 2002, provisional application No. 60/435,324, filed on Dec. 20, 2002, provisional application No. 60/468,979, filed on May 7, 2003, provisional application No. 60/469,053, filed on May 7, 2003, provisional application No. 60/533,891, filed on Dec. 31, 2003, provisional application No. 60/468,977, filed on May 7, 2003, provisional application No. 60/534,204, filed on Dec. 31, 2003, provisional application No. 60/574,733, filed on May 26, 2004, provisional application No. 60/533,932, filed on Dec. 31, 2003, provisional application No. 60/534,157, filed on Dec. 31, 2003, provisional application No. 60/533,891, filed on Dec. 31, 2003, provisional application No. 60/574,733, filed on May 26, 2004, provisional application No. 60/468,979, filed on May 7, 2003, provisional application No. 60/469,053, filed on May 7, 2003, provisional application No. 60/533,891, filed on Dec. 31, 2003, provisional application No. 60/392,531, filed on Jun. 27, 2002, provisional application No. 60/415,374, filed on Oct. 1, 2002, provisional application No. 60/464,504, filed on Apr. 21, 2003, provisional application No. 60/476,554, filed on Jun. 6, 2003, provisional application No. 60/338,638, filed on Dec. 3, 2001, provisional application No. 60/340,372, filed on Dec. 6, 2001, provisional application No. 60/379,133, filed on May 7, 2002, provisional application No. 60/379,182, filed on May 7, 2002, provisional application No. 60/379,184, filed on May 7, 2002, provisional application No. 60/415,374, filed on Oct. 1, 2002, provisional application No. 60/379,130, filed on May 7, 2002, provisional application No. 60/392,531, filed on Jun. 27, 2002, provisional application No. 60/379,184, filed on May 7, 2002, provisional application No. 60/392,531, filed on Jun. 27, 2002, provisional application No. 60/379,182, filed on May 7, 2002, provisional application No. 60/430,809, filed on Dec. 3, 2002, provisional application No. 60/379,133, filed on May 7, 2002, provisional application No. 60/379,130, filed on May 7, 2002.

(56) References Cited

OTHER PUBLICATIONS

Adam L. Cohen, et al., "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, Sep. 1999.

Adam L. Cohen, "Electrochemical Fabrication (EFABTM)", Chapter 19 of the MEMS Handbook, edited by Mohamed Gad-El-Hak, CRC Press, 2002, pp. 19/1-19/23.

"Microfabrication—Rapid Prototyping's Killer Application", Rapid Prototyping Report, CAD/CAM Publishing, Inc., Jun. 1999, pp. 1-5.

* cited by examiner

MICRO-SCALE AND MESO-SCALE HYDRAULICALLY OR PNEUMATICALLY POWERED DEVICES CAPABLE OF ROTATIONAL MOTION

RELATED APPLICATIONS

This application claims benefit of U.S. Nos. 61/018,255 filed Dec. 31, 2007, 61/018,229 filed Dec. 31, 2007, and 60/948,262 filed Jul. 6, 2007, and is a CIP of application Ser. No. 12/139,445 filed Jun. 13, 2008 now U.S. Pat. No. 8,241,228; the '445 application in turn is a CIP of 10/949,744 filed Sep. 24, 2004 now U.S. Pat. No. 7,498,714, 12/134,188 filed Jun. 5, 2008 now abandoned, 12/138,404 filed Jun. 12, 2008 now abandoned, 12/138,395 filed Jun. 12, 2008 now abandoned, and 11/441,578 filed May 26, 2006 now U.S. Pat. No. 7,674,361, and claims benefit of App. Nos. 60/968,863 filed Aug. 29, 2007, 60/943,817 filed Jun. 13, 2007, 60/951,711 filed Jul. 24, 2007; 60/968,042 filed Aug. 24, 2007; 61/018,283 filed Dec. 31, 2007; the '744 application claims benefit of 60/506,016 filed Sep. 24, 2003; the '188 application claims benefit of App. Nos. 60/942,200 filed Jun. 5, 2007, 60/943,310 filed Jun. 12, 2007, 60/949,850 filed Jul. 14, 2007, 60/951,711 filed Jul. 24, 2007, 60/968,042 filed Aug. 24, 2007; 61/018,283 filed Dec. 31, 2007, 60/945,570 filed Jun. 21, 2007; 60/951,707 filed Jul. 24, 2007; 60/968,043 filed Aug. 2, 2007; and 61/018,303 filed Dec. 31, 2007, and is a CIP of application Ser. No. 11/625,807 filed Jan. 22, 2007 now abandoned; the '404 application in turn claims benefit of App. Nos. 60/943,309 filed Jun. 12, 2007, and 60/968,882 filed Aug. 29, 2007; the '395 application is a CIP of 11/696,722 filed Apr. 4, 2007 now abandoned and claims benefit of U.S. App. No. 60/943,318 filed Jun. 12, 2007; the '578 application claims benefit of App. No. 60/685,130 filed May 26, 2005; the '807 application claims benefit of 60/761,401, filed Jan. 20, 2006, and is a CIP of 11/598,968 filed Nov. 14, 2006 now abandoned, 11/582,049 filed Oct. 16, 2006 now U.S. Pat. No. 7,686,770, 11/478,934 filed Jun. 29, 2006 now abandoned, 11/444,999 filed May 31, 2006 now abandoned; and 10/697,598 filed Oct. 29, 2003 now abandoned; the '722 application claims benefit of App. No. 60/789,378 filed Apr. 4, 2006, and is a CIP of application Ser. No. 11/582,049 filed Oct. 16, 2006 now U.S. Pat. No. 7,686,770; the '049 application claims benefit of App. No. 60/726,794 filed Oct. 14, 2005; the '968 application claims benefit to 60/736,961 filed Nov. 14, 2005, and 60/761,401 filed Jan. 20, 2006, and is a CIP of application Ser. No. 11/591,911 filed Nov. 1, 2006 now abandoned; the '934 application claims the benefit to App. No. 60/695,328 filed Jun. 29, 2005, and is also a CIP of application Ser. Nos. 10/697,597 filed on Oct. 29, 2003 now abandoned, 10/841,100 filed May 7, 2004 now U.S. Pat. No. 7,109,118, 11/139,262 filed May 26, 2005 now U.S. Pat. No. 7,501,328, and 11/029,216 filed Jan. 3, 2005 now abandoned; the '999 application claims benefit of App. No. 60/686,496 filed May 31, 2005 and is a CIP of application Ser. No. 10/697,598 filed Oct. 29, 2003 now abandoned; the '598 application claims benefit of App. No. 60/422,007 filed Oct. 29, 2002; the '911 application claims benefit of App. Nos. 60/732,413 filed Nov. 1, 2005; 60/736,961 filed Nov. 14, 2005; and 60/761,401 filed Jan. 20, 2006; the '597 application claims benefit to App. No. 60/422,008 filed Oct. 29, 2002 and to App. No. 60/435,324 filed Dec. 20, 2002; the '100 application claims benefit of App. 60/468,979 filed May 7, 2003; 60/469,053 filed May 7, 2003; 60/533,891 filed Dec. 31, 2003; 60/468,977 filed May 7, 2003; and 60/534,204 filed Dec. 31, 2003; the '262 application claims benefit of App. No. 60/574,733 filed May 26, 2004 and is a CIP of application Ser. No. 10/841,383 filed May 7, 2004 now U.S. Pat. No. 7,195,989; the '216 application claims benefit of App. Nos. 60/533,932, 60/534,157, 60/533,891, and 60/574,733, filed on Dec. 31, 2003, Dec. 31, 2003, Dec. 31, 2003, and May 26, 2004 and is a CIP of application Ser. Nos. 10/841,300 now abandoned, and 10/607,931 now U.S. Pat. No. 7,239,219 filed on May 7, 2004 and Jun. 27, 2003, respectively; the '383 application claims benefit to App. 60/468,979 filed May 7, 2003; 60/469,053 filed May 7, 2003; and 60/533,891 filed Dec. 31, 2003; the '300 application claims benefit of App. 60/468,979 filed May 7, 2003; 60/469,053 filed May 7, 2003; and 60/533,891 filed Dec. 31, 2003; and the '931 application claims benefit of App. Nos. 60/392,531 filed Jun. 27, 2002; 60/415,374 filed Oct. 1, 2002; 60/464,504 filed Apr. 21, 2003; and 60/476,554 filed on Jun. 6, 2003; the '931 application is also a CIP of application Ser. Nos. 10/309,521 filed on Dec. 3, 2002; and 10/434,497 now U.S. Pat. No. 7,303,663, 10/434,103 now U.S. Pat. No. 7,160,429, 10/434,295 now abandoned, and 10/434,519 now U.S. Pat. No. 7,252,861, each filed on May 7, 2003; the '521 application in turn claims benefit of App. Nos. 60/338,638 filed on Dec. 3, 2001; 60/340,372 filed on Dec. 6, 2001; 60/379,133 filed on May. 8, 2002; 60/379,182 filed on May 7, 2002; 60/379,184 filed on May 7, 2002; 60/415,374 filed on Oct. 1, 2002; 60/379,130 filed on May 7, 2002 and 60/392,531 filed on Jun. 27, 2002; the '497 application in turn claims benefit of App. Nos. 60/379,184 filed May 7, 2002; and 60/392,531 filed Jun. 27, 2002; the '103 application in turn claims benefit of App. Nos. 60/379,182 filed May 7, 2002, and 60/430,809 filed Dec. 32, 2002; the '295 application in turn claims benefit of App. No. 60/379,133 filed May. 8, 2002; and the '519 application in turn claims benefit of App. No. 60/379,130 filed May 7, 2002. Each of these applications is incorporated herein by reference as if set forth in full herein.

FIELD OF THE INVENTION

The present invention relates generally to the field of micro-scale and meso-scale devices (e.g. medical devices) and to the use of multi-layer multi-material electrochemical fabrication methods for producing such devices, particular embodiments relate to hydraulic and/or pneumatic devices while others relate more specifically to medical tools that may be useful in medical procedures and in particular for minimally invasive medical procedures.

BACKGROUND OF THE INVENTION

Electrochemical Fabrication

Electrochemical Fabrication:

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allow the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING™ or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p161, August 1998.
(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p244, January 1999.
(3) A. Cohen, "3-D Micromachining by Electrochemical Fabrication", Micromachine Devices, March 1999.
(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.
(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.
(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.
(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.
(8) A. Cohen, "Electrochemical Fabrication (EFABTM)", Chapter 19 of The MEMS Handbook, edited by Mohamed Gad-El-Hak, CRC Press, 2002.
(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.
2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.
3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i.e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

SUMMARY OF THE INVENTION

It is an object of some embodiments of the invention to provide improved micro-scale or meso-scale hydraulic or pneumatic devices that include miniature bearing and race elements.

It is an object of some embodiments of the invention to provide improved micro-scale or meso-scale hydraulic or pneumatic turbine devices.

It is an object of some embodiments of the invention to provide improved micro-scale or meso-scale hydraulic or pneumatic tools that may be used in medical applications and particularly in medical applications where the tools are located at the distal end of a larger device which traverses a torturous path and which may supply rotary or other movement without the need for movement of pull wires or push tubes or the like and without the need for locating electrical motors at the distal end of the device.

It is an object of some embodiments of the invention to provide improved methods for fabricating micro-scale or meso-scale devices.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

A first aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process.

Numerous variations of the first aspect of the invention are possible and may include for example the following features: (1) use of the device in a medical procedure; (2) use of the device in a minimally invasive medical procedure; (3) the passage is configured to cause fluid flow from the stator to the rotor to be from one or more radial positions that are further from the rotational axis while fluid flow from the rotor will begin at one or more radial positions that are closer to the rotational axis; (4) the passage is configured to cause fluid flow from the stator to the rotor to be from one or more radial positions that are closer to the rotational axis while fluid flow from the rotor will begin at one or more radial positions that are further from the rotational axis; (5) at least one bearing element is located within a slot in the rotor and against a substantially planar surface or the stator; (6) at least one bearing element is located within a slot in the stator and against a substantially planar surface or the rotor; (7) the rotor includes at least one opening for loading bearing elements into desired positions between the rotor and the stator wherein the rotor additionally includes a catch that holds the bearing elements in between the rotor and stator after loading; (8) the rotor comprises a cutting blade; (9) the rotor comprises a blending tool; (9) the stator includes at least one opening for loading bearing elements into desired positions between the rotor and the stator wherein the stator additionally includes a catch that holds the bearing elements in between the rotor and stator after loading; (10) the passage is configured to cause fluid flow from the stator to the rotor to be from one or more radial positions that are closer to the rotational axis while fluid flow from the rotor will begin at one or more radial positions that are further from the rotational axis; (11) the rotor additionally comprises a coupling element that is capable of accepting different tools which are turned by the device. (12) the rotor additionally comprises a fixed tool.

A second aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow.

Another variation of the first aspect of the invention includes at least a portion of the bearing elements being formed using a multi-layer, multi-material electrochemical fabrication process while a further variation includes the stator bearing surface having protrusions and indentations, wherein the rotor includes a rotor bearing surface having protrusions and indentations, and wherein the bearing elements comprise outer surface protrusions and indentations and wherein during formation, at least some protrusions on the stator bearing surface and on the rotor bearing surface align with indentations on the outer surface of the bearing elements and wherein at least some indentations on the rotor bearing surface and on the stator bearing surface align with protrusions on the outer surface of the bearing elements, such that gaps between the bearing elements and the rotor and stator bearing surfaces on any given layers are larger than a minimum feature size but wherein on at least adjacent layers, gaps are substantially less than the minimum feature size.

Numerous variations of the second aspect of the invention are possible and may include for example the following features: (1) the bearing elements are balls; (2) the bearing elements are cylindrical rollers. (3) the device is a turbine and wherein fluid just before striking a blades is in a first direction and wherein after striking the blade continued fluid flow is in a substantially different direction and wherein a direction of fluid flow just before striking a blade may be perpendicular to the axis of rotation and after striking the blade the direction of fluid flow may be substantially axial; (4) the stator includes a manifold for directing fluid flow on to the blades from a plurality of locations; or (5) the stator includes a manifold for directing fluid flow on to the blades from a plurality of locations and each of the plurality of locations have orientation for directing a flow of fluid and wherein one of the following condition may be met: (i) the plurality of blades of the rotor are spaced with a uniform spacing angular spacing around the axis of rotation and wherein a spacing of the plurality of locations is different from the uniform spacing of the blades, or (ii) at least one of the plurality of locations has a different relative radial orientation than that of another location of the plurality of locations.

A third aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow, wherein the bearing elements are positioned around the axis of rotation at one or more bearing heights while the blades are positioned around the axis of rotation at one or more blade heights.

Numerous variations of the third aspect of the invention are possible and may include for example the following features: (1) one or more bearing heights are two or more bearing heights and they are located above and below the one or more blade heights; (2) one or more blade heights are two or more blade heights and they are located above and below the one or more bearing heights; or (3) the one or more bearing heights and the one or more blade heights share a common height.

A fourth aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow, wherein the bearing elements are positioned around the axis of rotation at one or more bearing heights while the blades are positioned around the axis of rotation at one or more blade heights.

A fifth aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow, wherein at least one bearing element is located within a slot in the rotor and a slot in the stator.

Numerous variations of the fifth aspect of the invention are possible and may include for example the following features: (1) the slot in the rotor faces radially outward and the slot in the stator faces radially inward; (2) the slot in the rotor faces radially inward and the slot in the stator faces radially outward; (3) the slot in the rotor faces axially upward and the slot in the stator faces radially downward; or (4) at least two rotor slots and at least two stator slots exist wherein the two rotor slots face in opposite directions and the two stator slots face in opposite directions.

A sixth aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow, wherein the stator includes at least one opening for loading bearing elements into desired positions between the rotor and the stator wherein the stator additionally includes a stator bearing surface of desired configuration along which the bearing elements move, wherein the device additionally includes a plug having a plug bearing surface of desired configuration which is matched to that of the desired configuration of stator bearing surface, wherein upon loading the bearings and inserting and fixing the plug to the stator, the plug bearing surface and the stator bearing surface provide for smooth movement of the bearing elements.

Numerous variations of the sixth aspect of the invention are possible and may include for example the following features: (1) neither the stator bearing surface nor the plug bearing surface are planar; (2) the stator or plug includes a stop feature that ensures that the plug and stator are located in desired relative positions once assembled; (3) the stator or plug further comprises a locking mechanism for holding the stator and plug together; or (4) the stator and plug are held together by a bonding agent after being inserted into desired relative positions.

A seventh aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least a portion of the stator and the rotor are formed using a multi-layer, multi-material electrochemical fabrication process, wherein the rotor includes plurality of blades which are moved by the fluid flow, wherein the rotor includes at least one opening for loading bearing elements into desired positions between the rotor and the stator wherein the rotor additionally includes a rotor bearing surface of desired configuration along which the bearing elements move, wherein the device additionally includes a plug having a plug bearing surface of desired configuration which is matched to that of the desired configuration of rotor bearing surface, wherein upon loading the bearings and inserting and fixing the plug to the rotor, the plug bearing surface and the rotor bearing surface provide for smooth movement of the bearing elements.

Numerous variations of the seventh aspect of the invention are possible and may include for example the following features: (1) neither the rotor bearing surface nor the plug bearing surface are planar; (2) the rotor or plug includes a stop feature that ensures that the plug and stator are located in desired relative positions once assembled; (3) the rotor or plug further comprises a locking mechanism for holding the rotor and plug together; or (4) the rotor and plug are held together by a bonding agent after being inserted into desired relative positions.

An eighth aspect of the invention provides a device capable of converting a flow of a driving fluid into rotational mechanical motion, comprising: (a) a stator; (b) a rotor capable of rotational motion relative to the stator, wherein the rotational motion occurs about a rotational axis; (c) spacings formed between a lower axial facing surface of the rotor and an upper axial facing surface of the stator, and between an upper axial facing surface of the rotor and a lower axial facing surface of the stator; and between radial facing surfaces of the stator and the rotor; (d) an inlet in said stator for receiving a driving fluid and an outlet in said stator for removing the driving fluid; (e) one or more channels for carrying a bearing fluid to the said spacings such that the bearing fluid may provide a hydrostatic bearing effect; and wherein at least a portion of each of the stator, the rotor, the spacings, and the one or more channels are formed using a multi-layer, multi-material electrochemical fabrication process.

A ninth aspect of the invention provides a device capable of converting a flow of a fluid into rotational mechanical motion, comprising: (a) a stator; (b) a rotor capable of rotational motion relative to the stator, wherein the rotational motion occurs about a rotational axis; (c) a plurality of bearing elements positioned between the rotor and stator to hold the rotor and the stator in desired relative positions; (d) an inlet in said stator for receiving a fluid and an outlet in said stator for removing fluid; wherein at least portions of the stator and the rotor are formed from multiple layers of deposited materials while in assembled positions relative to one another.

A tenth aspect of the invention provides a device capable of converting a flow of a fluid into rotational mechanical motion, comprising: (a) a stator comprising a stator bearing surface including a plurality of protrusions extending in a radial direction separated by recesses that are indented relative to adjacent protrusions; (b) a rotor capable of rotational motion relative to the stator, wherein the rotational motion occurs about a rotational axis and wherein the rotor comprises a rotor bearing surface including a plurality of protrusions extending in a radial direction separated by recesses that are indented relative to adjacent protrusions; (c) a plurality of bearing elements positioned between the rotor and stator to hold the rotor and the stator in desired relative positions and wherein the bearing elements comprise an outer surface including a plurality of protrusions separated by recesses that are indented relative to adjacent protrusions; (d) an inlet in said stator for receiving a fluid and an outlet in said stator for removing fluid; wherein during formation, at least some protrusions on the stator bearing surface and on the rotor bearing surface align with indentations on the outer surface of the bearing elements and wherein at least some indentations on the rotor bearing surface and on the stator bearing surface align with protrusions on the outer surface of the bearing elements, such that gaps between the bearing elements and the rotor and stator surface on any given layer are larger than a minimum feature size but wherein on at least some adjacent layers, gaps are substantially less than the minimum feature size.

An eleventh aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) one or more ball bearings loaded into one or more openings in one or more components and which optionally may become trapped within desired locations in the component(s) when components of the device are maintained within a working range of the device.

A twelfth aspect of the invention provides a method for fabricating a rotary device, comprising: (a) forming at least a portion of a stator and a rotor from a plurality of adhered layers of material wherein the stator comprises a stator bearing surface, wherein the rotor comprises a rotor bearing surface, and wherein the forming of each layer of material comprises, (i) depositing of at least a first material; (II) depositing of at least a second material; and (iii) planarizing the first and second materials to a common level; (b) removing of at least a portion of the first or second material after formation of the plurality of layers; (c) supplying a plurality of bearing elements; (d) inserting the bearing elements into an opening between the stator bearing surface and the rotor bearing surface.

Numerous variations of the twelfth aspect of the invention are possible and may, for example, include the following features: (1) the bearing elements are inserted after formation of the stator and rotor are completed; (2) forming of the at least one additional layer to complete formation of the stator and the rotor, after inserting the bearing elements, wherein the forming of the at least one additional layer comprises: (i) deposition of at least a first material; (ii) deposition of at least a second material; and (iii) planarizing the first and second materials to a common level; and (f) removing of at least a portion of the first or second material after formation of the at least one additional layer; (3) the stator and the rotor are formed in substantially assembled positions relative to each other; or (4) the stator and the rotor are formed separately from one another and are thereafter inserted into assembled positions and bearing elements are inserted; or (5) the forming of the plurality of adhered layers comprises forming lower portions of the stator and rotor in assembled positions forming upper portions of the stator and rotor in assembled positions but laterally spaced from the lower portions and upside down relative to the lower portions and wherein the method additionally includes removing sacrificial material from inside a gap region on the lower portions intended to receive bearing elements and a gap region on the upper portions intended to receiving bearing elements, applying bearing elements into at least one of the gap region in the lower portion or in the upper portion and then bringing a mating surface of the lower portion and a mating surface of the upper portion into desired relative positions and affixing the lower portions and upper portions together (e.g. via use of a bonding material or via one or more catches formed along with one or both of the lower portion and the upper portion).

A thirteenth aspect of the invention provides a method for fabricating a rotary device, comprising: (a) forming at least a portion of a stator, a rotor, and a plurality of bearing elements from a plurality of adhered layers of material wherein the stator comprises a stator bearing surface including a plurality of protrusions separated by indentations, wherein the rotor comprises a rotor bearing surface including a plurality of protrusions separated by indentations, and wherein the bearing elements comprise an outer surface including a plurality of protrusions separated by indentations, and wherein the forming of each layer of material comprises: (i) deposition of at least a first material; (ii) deposition of at least a second material; and (iii) planarizing the first and second materials to a common level; (b) removing of at least a portion of the first or second material after formation of the plurality of layers; and (c) supplying a plurality of bearing elements, and wherein during formation, at least some protrusions on the stator bearing surface and on the rotor bearing surface align with indentations on the outer surface of the bearing elements and wherein at least some indentations on the rotor bearing surface and on the stator bearing surface align with protrusions on the outer surface of the bearing elements, such that gaps between the bearing elements and the rotor and stator surface on any given layer are larger than a minimum feature size but wherein on at least some adjacent layers, gaps are substantially less than the minimum feature size.

A fourteenth aspect of the invention provides a method for fabricating a rotary device, comprising: (a) forming at least a portion of a stator and a rotor from a plurality of adhered layers, each comprising at least one sacrificial material and at least one structural material, including forming: (1) an inlet for receiving a driving fluid, (2) an outlet, (3) a passage connecting the inlet and outlet together along which the driving fluid may flow to cause movement of the rotor relative to the stator; (4) spacings between a lower axial facing surface of the rotor and an upper axial facing surface of the stator, and between an upper axial facing surface of the rotor and a lower axial facing surface of the stator; and between radial facing surfaces of the stator and the rotor, and forming one or more channels for carrying a bearing fluid to the spacings such that bearing fluid may provide a hydrostatic bearing effect during operation of the device; and wherein the forming of each multi-material layer comprises: (i) deposition of at least a first material; (ii) deposition of at least a second material; and (iii) planarizing the first and second materials to a common level; and (b) removing of at least a portion of the first or second material after formation of the plurality of layers.

A fifteenth aspect of the invention provides a minimally invasive medical procedure for providing a diagnostic, preventive, or therapeutic treatment to a body of a patient (i.e. a medically useful procedure), comprising: (a) inserting a lumen, having a distal and proximal end into the body of a patient such that the proximal end remains outside the body of the patient while the distal end is located in proximity to a desired location within the body of the patient; (b) inserting a device into the lumen to provide the diagnostic, preventive, or therapeutic treatment to a desired site within the body of the patient; (c) while at the desired site, operating the device to provide or aid in the provision of the diagnostic or therapeutic treatment wherein the device of one of the first through eleventh aspects of the invention or wherein the device is fabricated by one of the twelfth through fourteenth aspects of the invention.

Numerous variations of the fifteenth aspect of the invention exist and may, for example, include the following features: (1) the desired location is located at the end of a torturous path that is traversed to locate the device at the desired location wherein a rotary motion of the rotor relative to the stator occur via a fluid flow; (2) the procedure comprises a thrombectomy procedure; (3) the procedure comprises an atherectomy procedure; (3) the procedure comprises an ultrasound procedure; or (4) the procedure comprises a dental procedure for at least one of (a) removing decayed tooth material, (b) debriding and cleaning, (c) in preparation for cavity filling, or (4) in performing a root canal obturation.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 17A and 7B provide top and bottom perspective views of a turbine of a sixth embodiment of the invention which is similar to that of the embodiment of FIGS. 5-11 with the exception that the cutting tool is replaced by a coupling that can accept different tools while FIG. 17C provides a cut perspective view of the turbine of FIGS. 17A and 17B prior to the loading of ball bearing into the bearing race.

DETAILED DESCRIPTION OF PREFERRED EMBODIMENTS

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 1A:
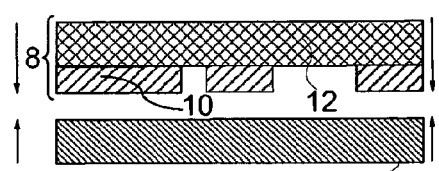
FIGS. 1A-1C schematically depict side views of various stages of a CC mask plating process, while FIGS. 1D-G schematically depict a side views of various stages of a CC mask plating process using a different type of CC mask.
Figure 1B:
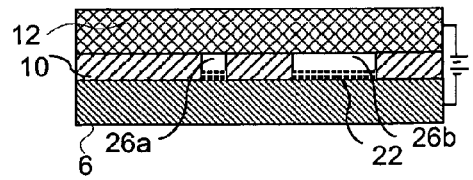
Figure 1C:
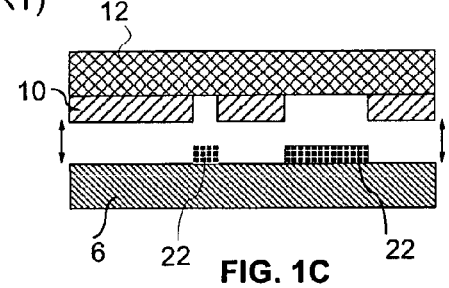
Figure 1D:
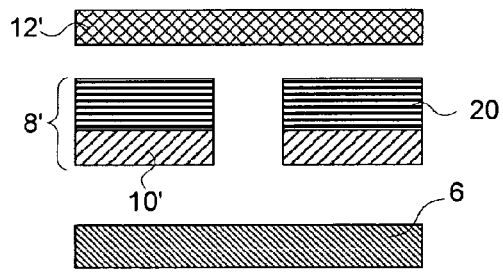
FIGS. 16A-1 to FIG. 16F illustrate various states in a method of embedding balls during fabrication of a turbine according to a fifth embodiment of the invention.
Figure 1E:
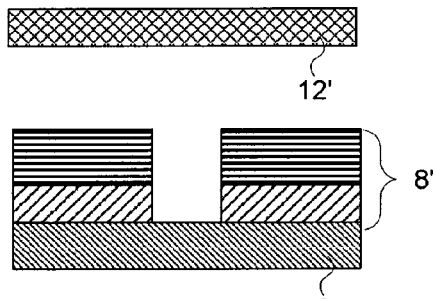
Figure 1F:
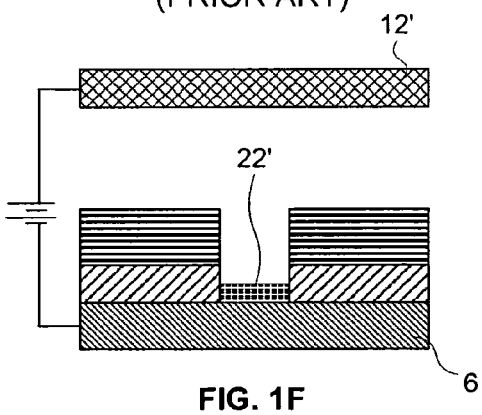
Figure 1G:
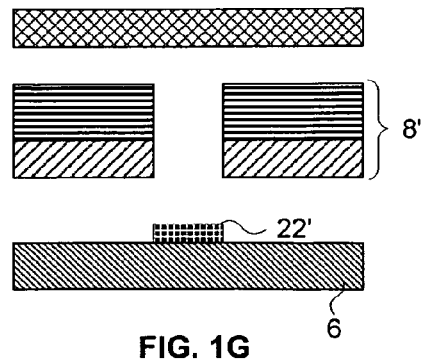
Figure 2A:
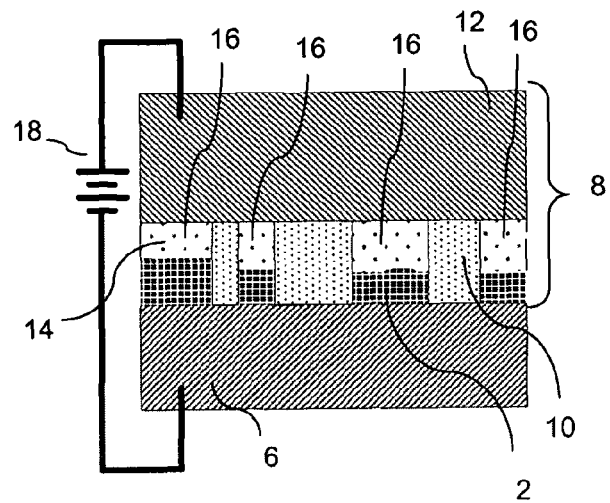
FIGS. 2A-2F schematically depict side views of various stages of an electrochemical fabrication process as applied to the formation of a particular structure where a sacrificial material is selectively deposited while a structural material is blanket deposited.
Figure 2B:
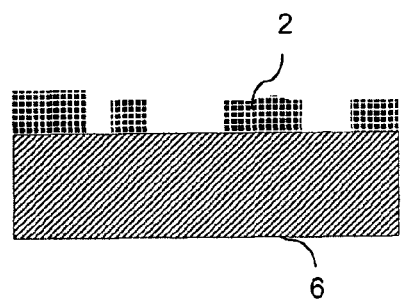
Figure 2C:
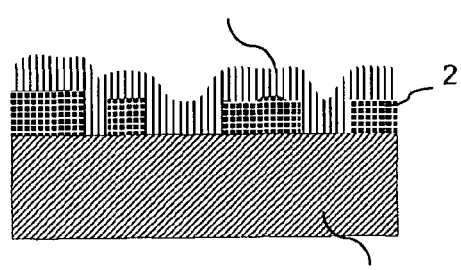
Figure 2D:
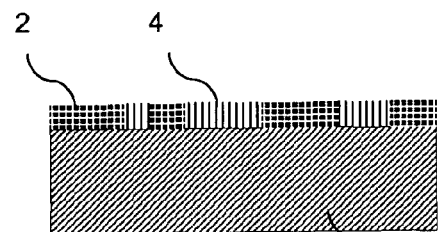
Figure 2E:
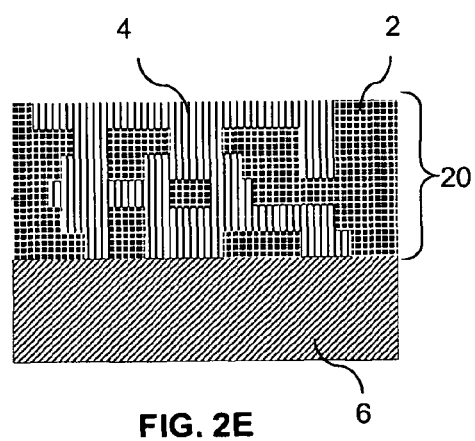
Figure 2F:
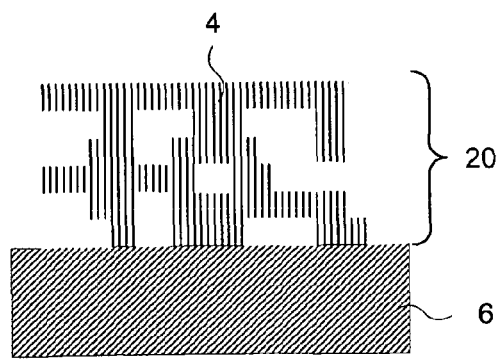
Figure 3A:
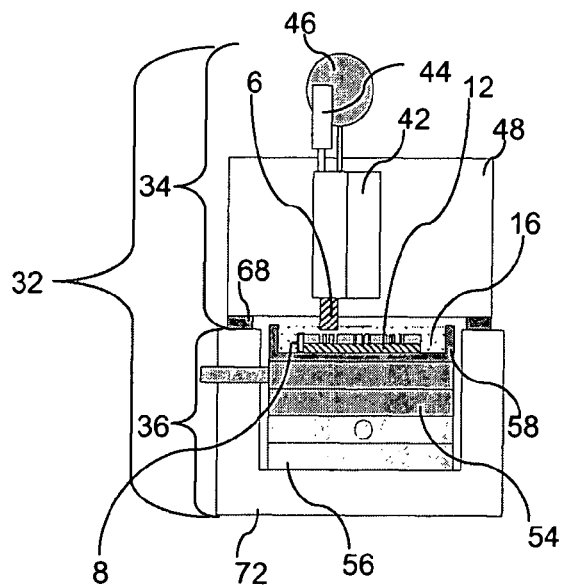
FIGS. 3A-3C schematically depict side views of various example subassemblies that may be used in manually implementing the electrochemical fabrication method depicted in FIGS. 2A-2F.
Figure 3B:
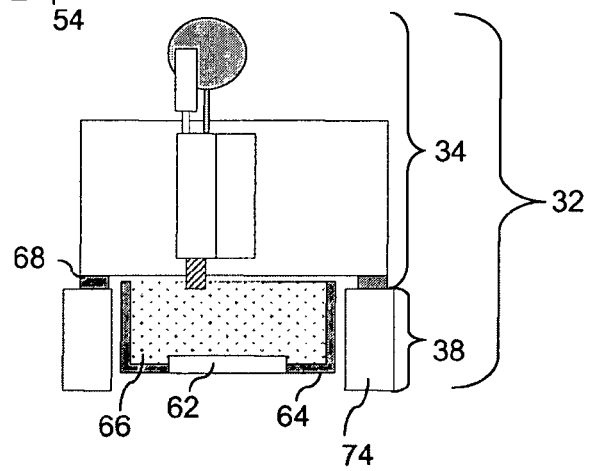
Figure 3C:
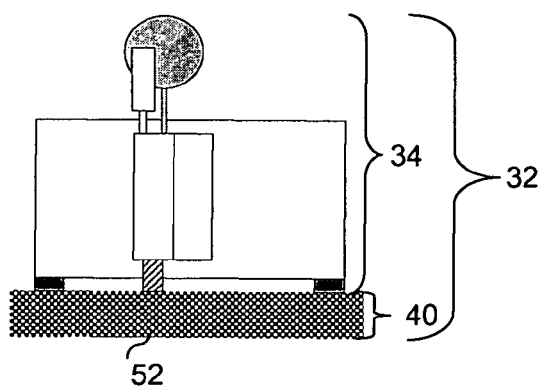
Figure 4A:
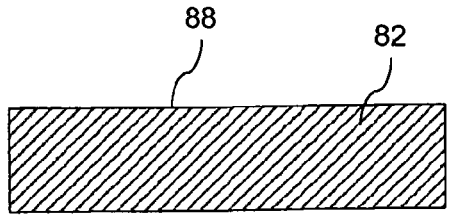
FIGS. 4A-4F schematically depict the formation of a first layer of a structure using adhered mask plating where the blanket deposition of a second material overlays both the openings between deposition locations of a first material and the first material itself
Figure 4B:
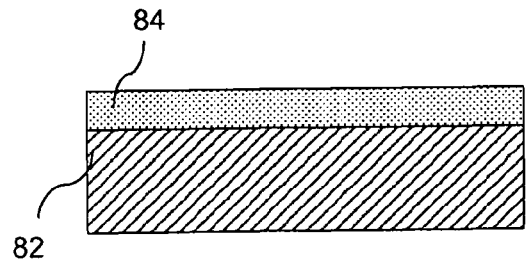
Figure 4C:
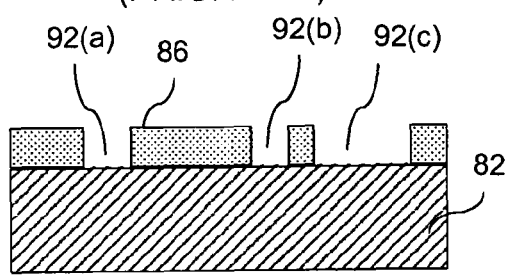
Figure 4D:
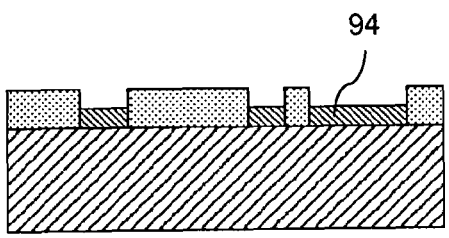
Figure 4E:
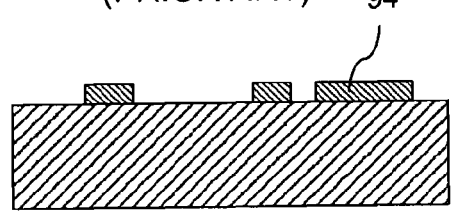
Figure 4F:
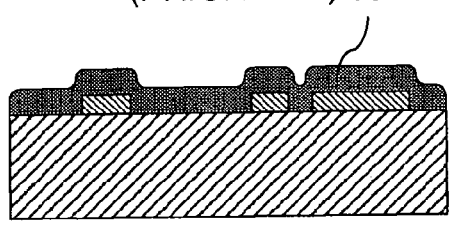
Figure 4G:
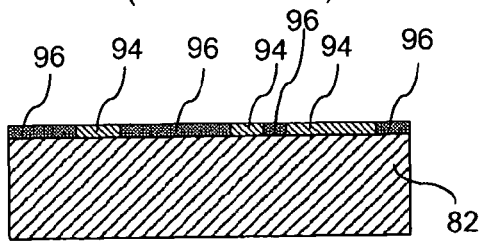
FIG. 4G depicts the completion of formation of the first layer resulting from planarizing the deposited materials to a desired level.
Figure 4H:
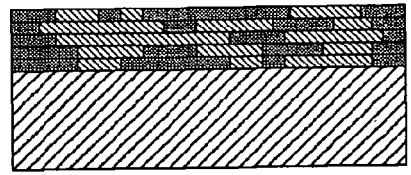
FIGS. 4H and 4I respectively depict the state of the process after formation of the multiple layers of the structure and after release of the structure from the sacrificial material.
Figure 4I:
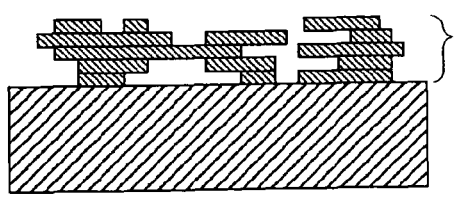

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4G several times to form a multi-layer structure are shown where each layer consists of two materials. For most applications, one of these materials is removed as shown in FIG. 4I to yield a desired 3-D structure 98 (e.g. component or device).

Various embodiments of various aspects of the invention are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable.

The various embodiments, alternatives, and techniques disclosed herein may form multi-layer structures using a single patterning technique on all layers or using different patterning techniques on different layers. For example, Various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. patent application Ser. No. 10/434,519, by Smalley, and entitled "Methods of and Apparatus for Electrochemically Fabricating Structures Via Interlaced Layers or Via Selective Etching and Filling of Voids layer elements" which is hereby incorporated herein by reference as if set forth in full.

Temporary substrates on which structures may be formed may be of the sacrificial-type (i.e. destroyed or damaged during separation of deposited materials to the extent they can not be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

DEFINITIONS

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519. This referenced application is incorporated herein by reference as if set forth in full. In most embodiments, a build layer includes at least one primary structural material and at least one primary sacrificial material. However, in some embodiments, two or more primary structural materials may used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization maybe followed or proceeded by thermally induced planarization (.e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, barrier layer materials (e.g. diffusion barrier material), and the like. These secondary structural materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. In other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 $\mu m^2$) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 20% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. In other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "n".

"Minimum feature size" refers to a necessary or desirable spacing between structural material elements on a given layer that are to remain distinct in the final device configuration. If the minimum feature size is not maintained on a given layer, the fabrication process may result in structural material inadvertently bridging the two structural elements due to masking material failure or failure to appropriately fill voids with sacrificial material during formation of the given layer such that during formation of a subsequent layer structural material inadvertently fills the void. More care during fabrication can lead to a reduction in minimum feature size or a willingness to accept greater losses in productivity can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of sacrificial material regions. Conversely a minimum feature size for structure material regions (minimum width or length of structural material elements) may be specified. Depending on the fabrication method and order of deposition of structural material and sacrificial material, the two types of minimum feature sizes may be different. In practice, for example, using electrochemical fabrication methods and described herein, the minimum features size on a given layer may be roughly set to a value that approximates the layer thickness used to form the layer and it may be considered the same for both structural and sacrificial material widths and lengths. In some more rigorously implemented processes, examination regiments, and rework requirements, it may be set to an amount that is 80%, 50%, or even 30% of the layer thickness. Other values or methods of setting minimum feature sizes may be set.

Minimally Invasive Surgery or Procedures:

Various devices set forth in the embodiments of the invention may be used in the performance of medical procedures and particularly in the performance of procedures where very small tools are needed. Such procedures include various minimally invasive procedures where access to a desired working location in the body of a patient occurs via one or more lumens inserted through the skin or through a body cavity where tools, materials, and observations devices are inserted via the lumen(s). In some such procedures access to a desired location may be along a tortuous path. As used herein "tortuous path" refers to a path taken by the lumen which has turns or other obstacles which are numerous and/or sharp such a that a controlled and reliable manipulation of a tool or device at the distal end of the lumen via push tubes, pull wires, rotating cables, or the like, to achieve desired functions from manipulations at the proximal end of the lumen(s) is not achievable or at least not readily achievable by operators (surgeons, interventionalists, etc.) having reasonable skills and within reasonable or desirable time constraints and within reasonable risk limits.

Miniature Hydraulic and Pneumatic Rotary Devices:

Embodiments of the present invention provide hydraulic and/or pneumatic devices that may be used in different medical applications as well as in non-medical applications. Some embodiments of the invention are directed to miniature turbine devices that can be made to rotate by application of a fluid flow so as to provide rotational motive force on a small scale. By actuating the turbine of these embodiments with a fluid, the motive force can be delivered to locations that are difficult to access by other techniques. For example, an endoscopic application that uses a catheter for situating a medical tool through a tortuous path would be well served by such a device. A system that relies on spinning a wire inside the sheath of a catheter may be incapable of contending with a very tortuous path due to, e.g., increased friction on the drive wire. A fluid based system would have no such limitations. Even a tool at the distal end of such a device that is capable of converting back and forth linear motion of a wire may have difficulty reaching desired rotational velocities. Such devices may also be of particular use when the diameter or length of a distal tool makes it impractical to include an electrical motor of sufficient torque or rotational velocity.

It is envisioned that such devices may have numerous uses, including, for example:

(1) Thrombectomy devices: e.g., a turbine could drive a propeller or similar structure which could pull a thrombus into it and macerate it and/or which could create a vacuum that extracts the thrombus;

(2) Atherectomy devices: for conventional directional coronary atherectomy (DCA), atherectomy of the kind performed by the FoxHollow SilverHawk or by the Boston Scientific Rotablator;

(3) Intravascular ultrasound: spinning an ultrasound transducer at the distal end of the catheter. A similar application is optical coherence tomography (OCT) catheters where an optical element is spun.

(4). Dental: Removing decayed tooth material, debriding and cleaning, in preparation for cavity filling, root canal obturation, etc.

(5). Cardiac: Removing undesirable material such as extraneous muscle from the heart, calcium from heart valves, etc.

(6). Powering mechanisms (e.g., walking mechanisms which produce a 'gait' or rolling wheels) which can pull a guidewire through a hollow body structure, in lieu of pushing it.

(7). Self contained power sources when combined with a small compressed gas canister and a valve (e.g. by a membrane that is punctured when needed).

(8). Optical beam choppers (9) Optical scanners (for imaging, etc.)

(10) Cutting tools, regardless of specific application, where miniature saw blades, drill bits or end mill bits could provide useful service in small and/or hard to reach locations.

(12). More generally, turbines of the embodiments of the present invention may be used to drive any device that requires a spinning motive force or one that could convert a spinning motive force to the desired mode of motion.

(13). The turbines may be used to drive a mixing element for fluid mixing.

(14). The turbines may be used to create vibration by building them along with (or attaching them to) an eccentric mass. Vibration may be used to tunnel through chronic total occlusions, perform lithotripsy on kidney, ureteral, and gallstones, and for other purposes.

(15). Pairs of turbines may be used to form self-contained systems with only an electrical connection (e.g, an IVUS catheter). Such systems may incorporate a small motor at the proximal end driving one turbine-like device which is used as a pump, with a turbine at the distal end that is driven by the flow of liquid (e.g., saline). The pump and turbine can be connected by a catheter with at least two lumens, allowing fluid to move distally and then return.

(16). The turbines may be used as miniature flow meters or velocity sensors by allowing fluid flow to rotate the turbine in conjunction with one or more sensors that detect the movement of the rotor blades or of one or more elements that rotate along with the turbine. Such detection may occur optically, magnetically, resistively or the like.

Figure 5:
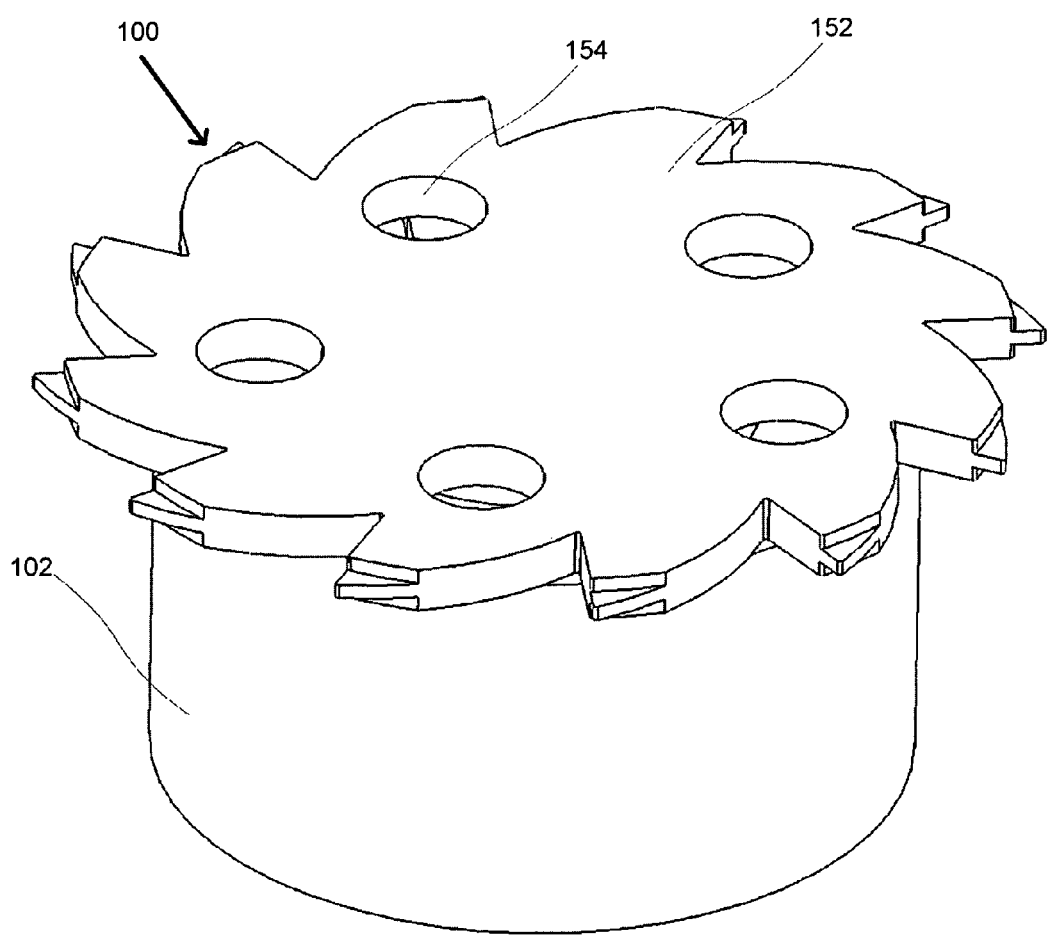
FIG. 5 provides a perspective view of a turbine according to a first embodiment of the invention which has a circular saw blade integrated with the rotor of the turbine.

FIG. 5 provides a perspective view of a turbine 100 according to a first embodiment of the invention. From this perspective, the housing of the turbine, or stator 102, and the cutting blade 152 may be seen. The cutting blade includes holes 154 which may help provide path-ways for etching away sacrificial material when the device is formed by one of the multi-layer, multi-material fabrications processes as taught herein. One or more such holes may also be used in combination with an appropriate sensor to provide feedback on angular rotation or rotational velocity during testing or operation of the device.

Figure 6:
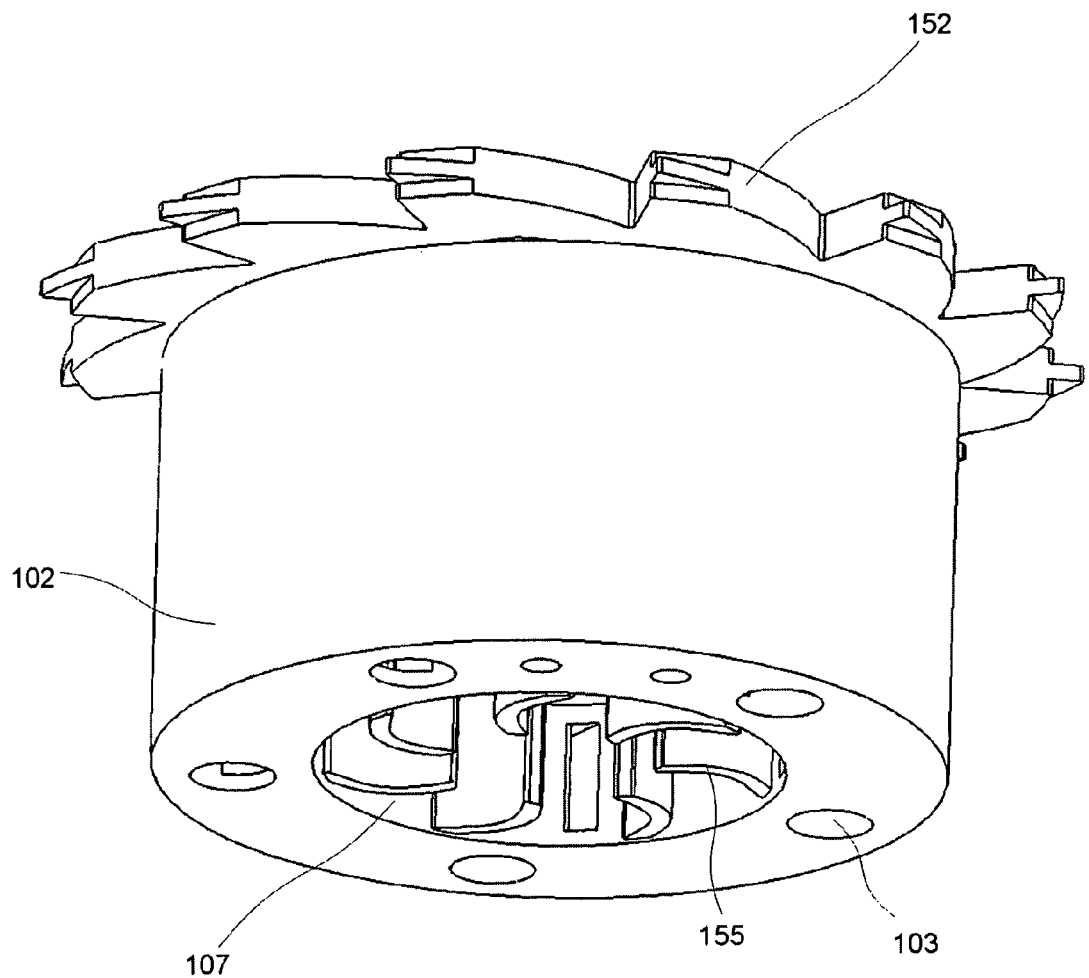
FIG. 6 provides a perspective view of the same device as FIG. 5 but from the fluid inlet and outlet side.

FIG. 6 provides a perspective view of the same device as FIG. 5 but from the fluid inlet and outlet side. In this figure the housing 102 and cutting blade 152 can still be seen but additionally the central fluid exit port 107 may be seen along with the fluid inlet ports 103 and turbine blades 155.

Figure 7:
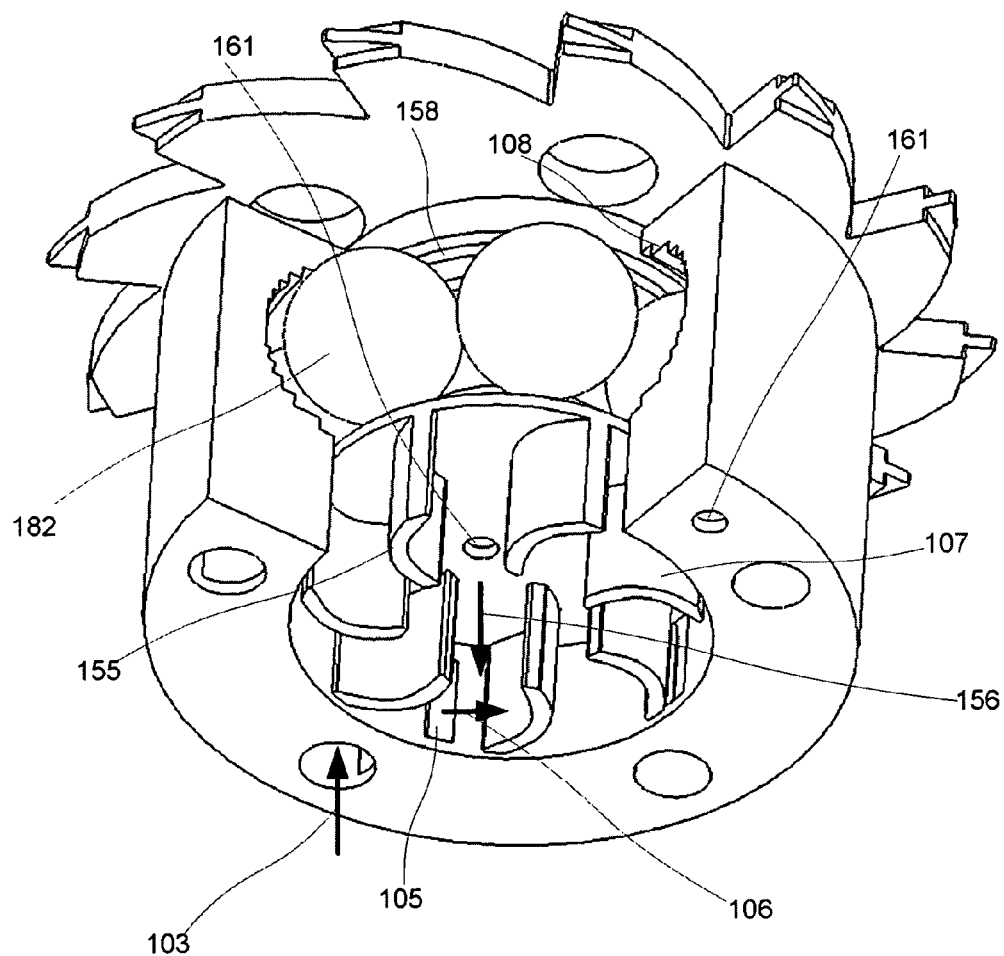
FIG. 7 provides a similar perspective to that of FIG. 6 but further includes a cut-away of the turbine housing or stator.

FIG. 7 provides a similar perspective to that of FIG. 6 but further includes a cut-away of the turbine housing or stator 102. This view allows the ball bearings 182 and the bearing races (i.e. rotor bearing surface and stator bearing surface to be seen along with a clearer view of the turbine blades 155. The races appear stepped due to the nature of the multi-layer, multiple material fabrication process that is assumed to be used in the formation of these portions of this device. There is also an indication of the fluid flow direction 106 toward the turbine blades. There are five inlets 103 in this embodiment (four can be seen in FIG. 7). The entire center aperture acts as an outlet 107 in this embodiment and it may be connected to a lumen of other tube for conveying the fluid away from the device site. There are also seven turbine blades shown in this embodiment. In this embodiment, the number of inlets differs from the number of turbine blades such that there is always a fluid flow that impinges on a turbine blade to cause a motive force. In other embodiments, the number of blades and inlets may be the same. In some alternatives, each inlet 103 may direct its flow of fluid into one or more stator exits 105 (i.e. ports that direct the fluid onto the rotor blades). In some alternatives the jetting directions from each exit port may have the same orientation with respect to the instantaneous radial direction while in other embodiments the orientations may be different. These variations may help ensure that the force distribution over a complete rotation is as uniform as possible. FIG. 7 also shows the direction of fluid as it is jetted out of the stator exit ports 105 to impinge on the turbine blade 155 by flow 106 after which the flow direction is axially downward out of the device as shown by arrow 156. In some variations of this embodiment the stator and the rotor may be formed separately along with other components and pairing marks such as those indicated by reference number 161 may be used to ensure proper elements are assembled together. In other embodiments they may be formed in substantially pre-assembled positions.

Figure 8:
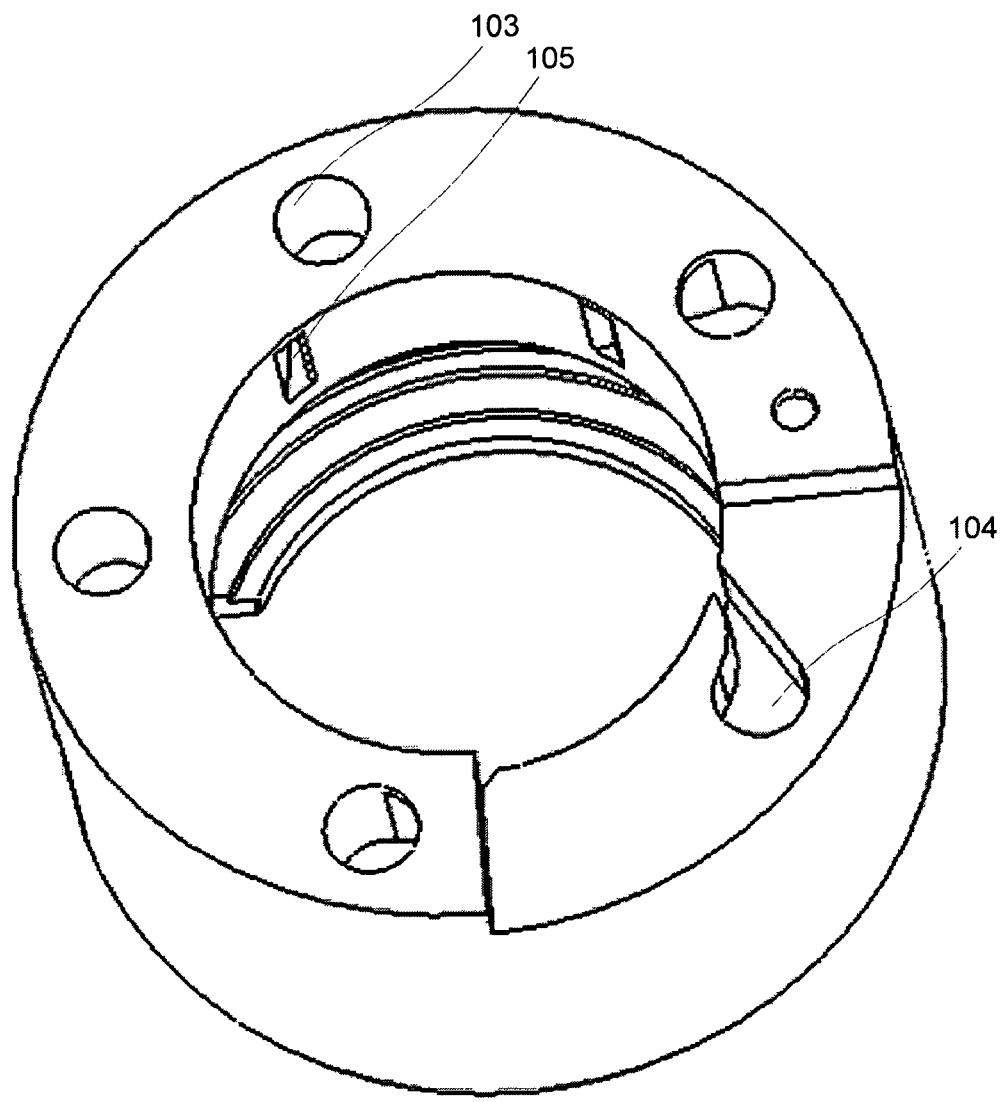
FIG. 8 provides a perspective cut away view of the bottom of the housing such that the channel connecting the fluid inlet to its respective outlet can be seen.

FIG. 8 provides a perspective cut away view of the bottom of the housing such that the channel 104 connecting the fluid inlet 103 to its respective outlet 105 can be seen. In this embodiment, the fluid is redirected from the inlet 103 to outlet 105 such that it impinges on the blades with a tangential velocity component. This turbine relies on impulse from the incoming fluid to drive the rotor. The pressure of the driving fluid does not change. It would also be possible to modify this design to what is known as a reaction turbine where the fluid pressure changes in the process of extracting energy from the fluid and driving the rotor. This type of turbine would more closely resemble the Francis turbine which is classically used for power generation.

Figure 9:
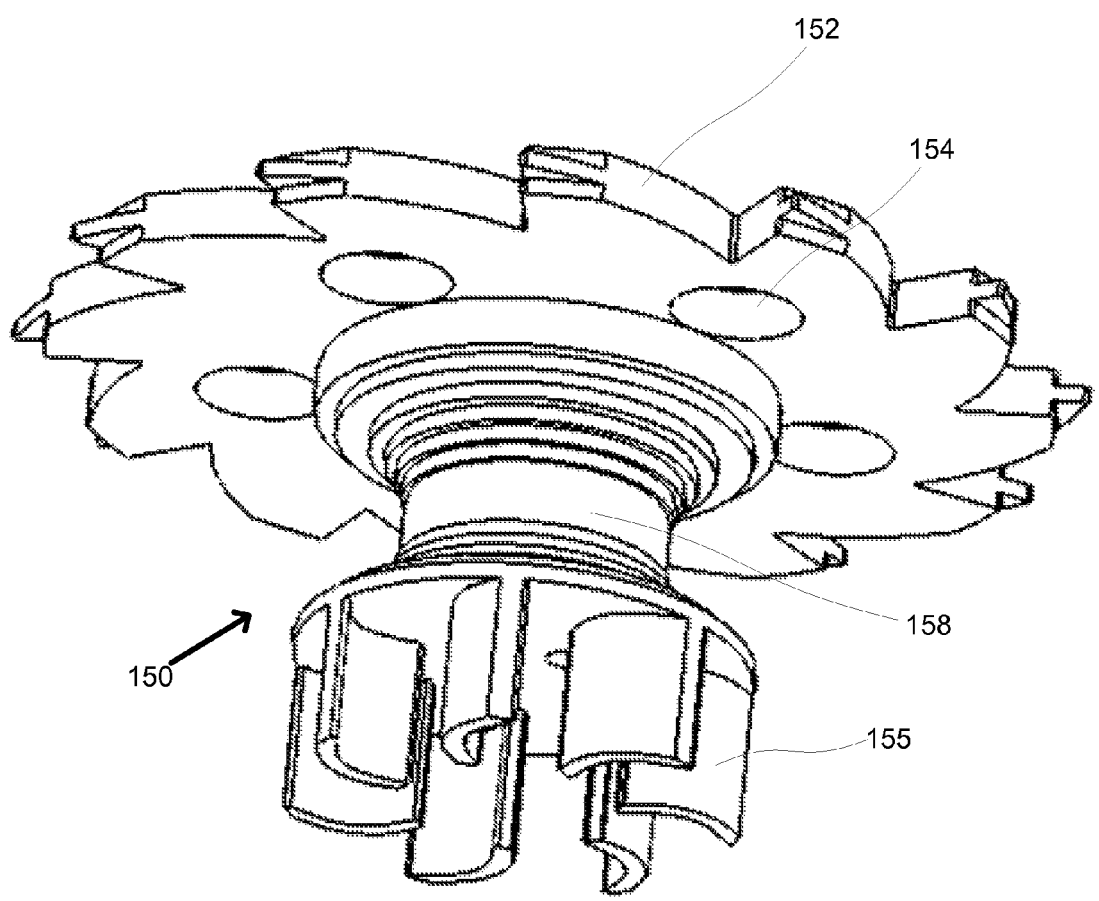
FIG. 9 provides a perspective view of the rotor so that the interior ball bearing race may be seen along with the rotor blades.

FIG. 9 provides a perspective view of the rotor 150 so that the interior ball bearing race 158 may be seen along with the rotor blades 155. These blades 155 are designed to extract the kinetic energy in the fluid flow while redirecting the fluid where it can exit from the center aperture of the turbine.

In addition to the various alternatives noted above a number of additional alternatives to this first embodiment are possible. For example the number of bearings, inlets, and turbine blades could be different. The shapes of the blade may be varied (e.g. to provide enhanced tangential thrust or even axial thrust. The blades may not be fully mounted to a base plate but instead may be created to provide some amount of compliant deflection under heavy loading conditions to provide an improved operational characteristic or overload protection. For example, the blade may be compliantly deflected to reduce flow by gaps which could improve efficiency or could increase gaps to provide reduced variation in rotational speed with changes in flow rate. In still other embodiments, a pair of turbines could be located on either side of the tool to provide increased driving power and more balanced tool operation. In still other embodiments a tool could be located on either side of the turbine blades with or without an additional set ball bearings and bearing races.

Figure 10:
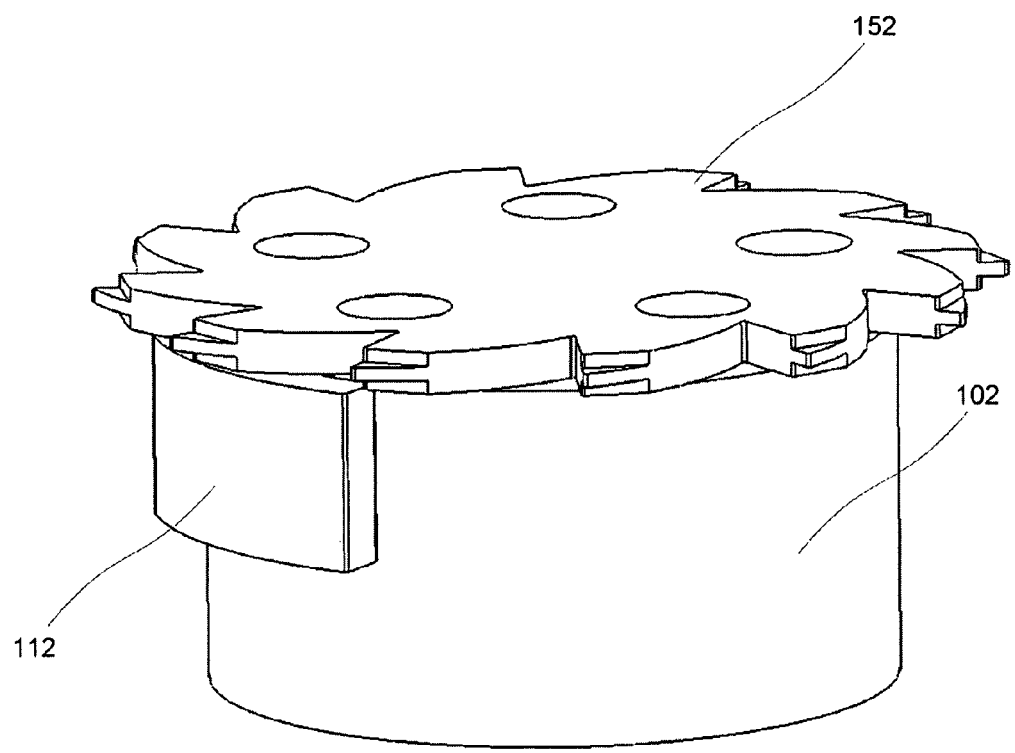
FIG. 10 provides a perspective view of the turbine with the plug inserted.
Figure 11:
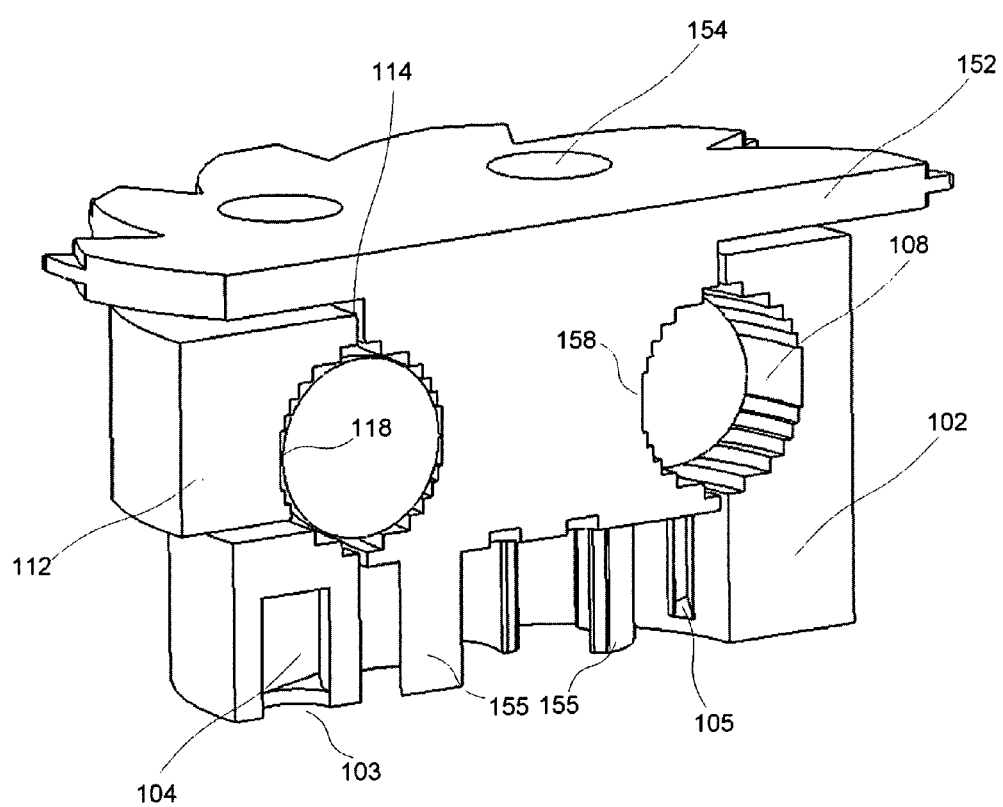
FIG. 11 provides a perspective cross sectional view of the assembly that includes a view of the plug showing its bearing race surface.

In this embodiment the turbine is built as a number of separate elements and then assembled. The separate parts of the turbine include the stator, the rotor which includes the saw blade, a plug, and a number of balls. The various parts of the turbine may be formed by the various multi-layer, multi-material build processes set forth herein or some of the parts, e.g. the balls, may be formed by other processes. The balls may be formed by one of the processes set forth herein potential in combination with one or more discontinuity reduction processes that smooth out the stair steps that typically accompany a multi-layer fabrication process. In the present embodiment, the ball bearings are added after the fabrication of the other parts is complete and they serve to constrain the rotor and stator relative to each other. Once the balls are inserted into the bearing cavity, they are constrained from coming back out by use of a plug that is fabricated with the stator (see FIG. 10). In the present embodiment the plug has a bearing race that matches the stator and it or the stator may have stops or other features that ensure proper positioning of the plug once it is inserted. The plug 112 is affixed to the stator 102 once it is located properly. The locking of the plug into place may occur by use of an adhesive, solder, epoxy, one or more mechanical catches or rings that may be formed along with the other parts. FIG. 10 provides a perspective view of the turbine with the plug 112 inserted. FIG. 11 provides a perspective cross sectional view of the assembly that includes a view of the plug 112 showing its bearing race surface 118 along with the bearing race surface 158 of the rotor and bearing race surface 108 of the stator 102.

In some alternative embodiments, the ball bearings and associated races may be replaced with cylindrical bearings, needle bearings, or other bearing elements, with or without spacing elements and with appropriate race configurations. These bearing may be inserted and locked into place during an assembly process after fabrication of the other components.

In still other alternative embodiments, the turbine and its various components may be fabricated in an assembled state. Such embodiments may include the use of ball bearings, cylindrical roller bearings, needle bearings, tapered roller bearings, thrust bearing, or the like. In such embodiments, special care may be taken to allow precision fitting of the bearing and race surfaces without violating minimum feature size rules that may exist as a result of the formation method chosen for fabricating the device. Examples of such "special" fabrication methods are provided in previously referenced U.S. Patent Application Nos. 60/943,817; 11/441,578; 10/949,744; and 12/139,445. In some such alternative embodiments, an axial shifting may be used to load the pre-assembled device from an as fabricated state to an operational state. Such shifting may result in a tightening of bearing to race gaps. Such shifting may occur prior to or as part of the initial configuration of the device or it may occur each time the device is operated. For example, the drive fluid may be directed at the blades such that it not only strikes the blades with a tangential component (and a radial component) but also with an axial component such that the rotor is provided with an axial component of force that can cause it to not only rotate radially but also be moved to a more optimal axial position. In some alternative embodiments interference bearing or bushing may be provided without need for layer shifting after formation of the devices. In still further embodiments, layer portions including interference bearing or bushing elements may be intentionally formed with excess stress so that slight distortions in layer positions occur after release of structure and so that more than edge to edge contact and stabilization occurs.

Figure 14:
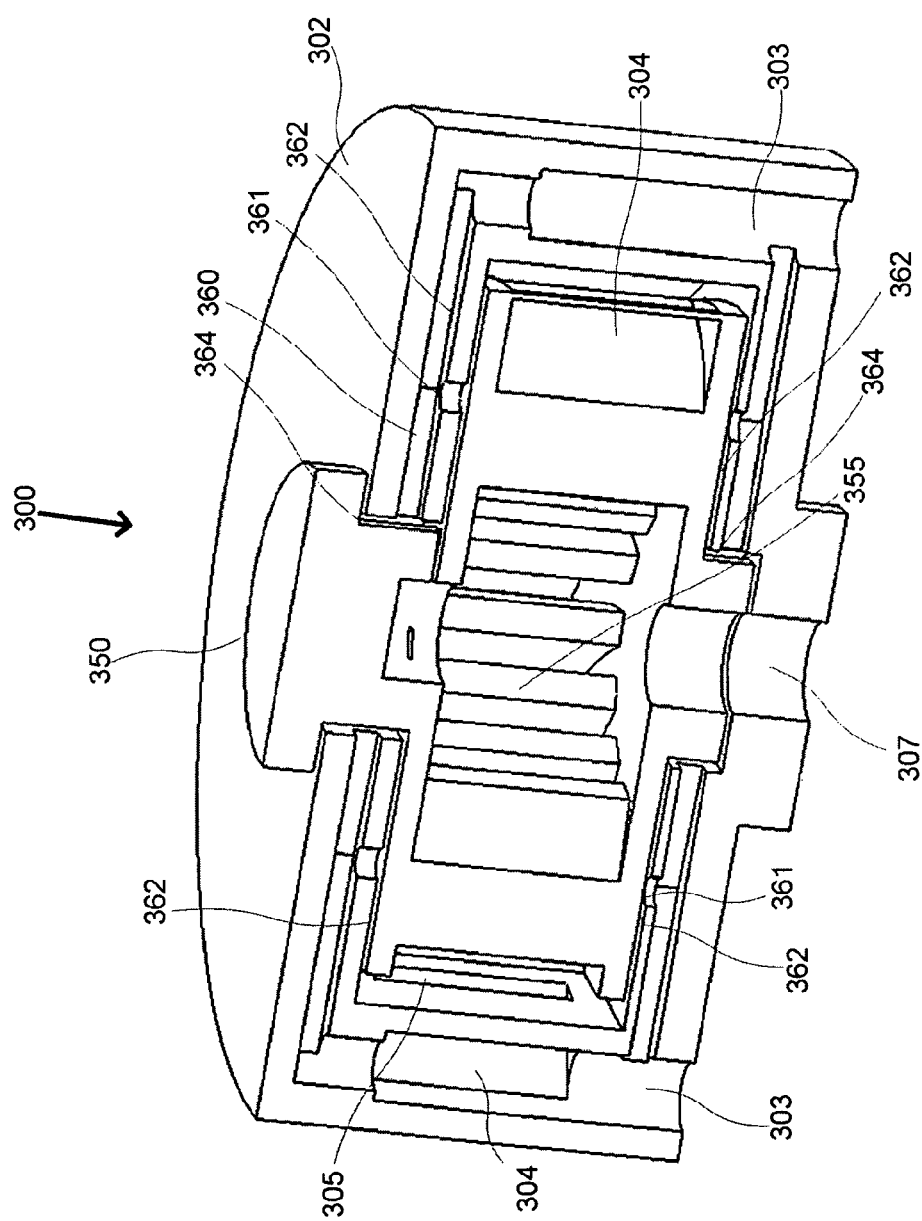
FIG. 14 provides a perspective view of an example turbine according to a third embodiment where hydrostatic or hydrodynamic fluid bearings are used to constrain the position of the rotor relative to the stator.

In some alternative embodiments, such as those that undergo slight shifting in the axially direction, fluid bearings may be used, either of the hydrostatic or hydrodynamic type to axially and radially constrain the rotor relative to the stator (see, for example, FIG. 14).

In this first embodiment of the turbine, the drive fluid enters the periphery of the back side of the device through the stator inlets 103, leaves the stator outlets 105 and flows 106 around the periphery of the back side to strike the rotor blades 155 and then is forced out 156 along the center of the backside. Thus the inlet 103 and outlet 107 are coaxial. In alternative embodiments, other inlet-outlet configurations are possible, e.g. the inlet may be on the proximal side of the device while the outlet may be on the distal side of the device. In various embodiments, the spent fluid may be recaptured or simply released.

Figure 12:
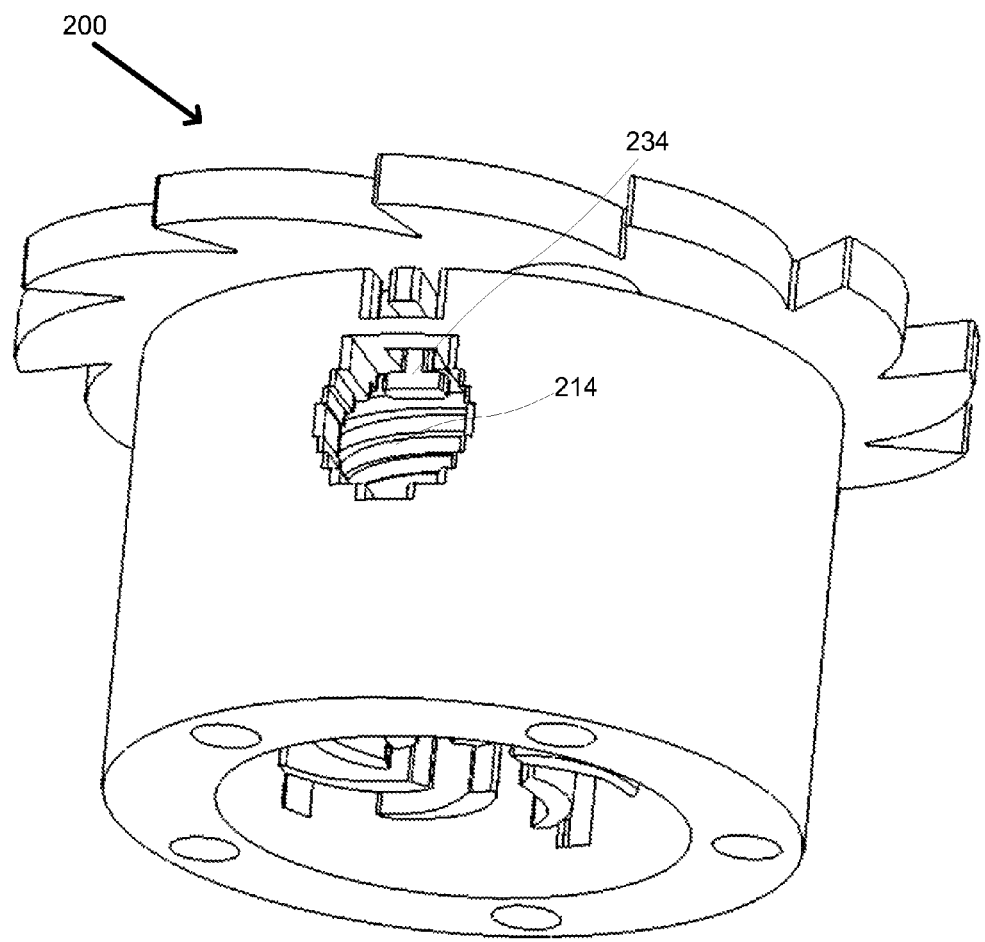
FIGS. 12 and 13 provide perspective view of a turbine device according to a second embodiment of the invention that includes an alternative mechanism for retaining the ball bearings.
Figure 13:
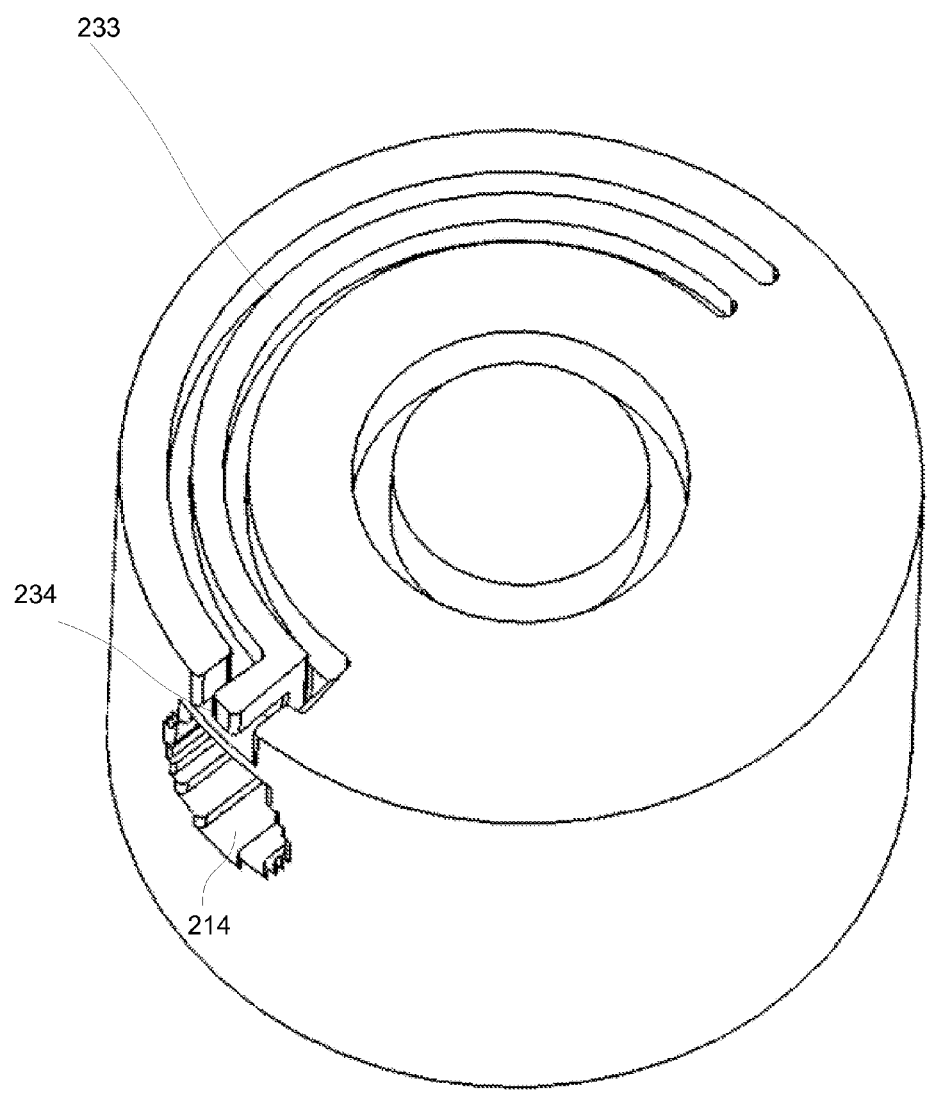

FIGS. 12 and 13 provide perspective views of a turbine device 200 according to a second embodiment of the invention that includes an alternative mechanism 234 for retaining the ball bearings 214. In this second embodiment, instead of using a plug, a leaf spring 233 is provided that includes a tab 234. When in its neutral position, the tab will prevent the ball bearings from coming out of the housing. The leaf spring allows the tab to be moved away from the neutral position for ball bearing insertion and removal.

FIG. 14 provides a perspective view of an example turbine 300 according to a third embodiment where hydrostatic or hydrodynamic vertical or axial facing fluid bearings 362 and radial facing bearings 364 are used to constrain the position of the rotor relative to the stator. In this embodiment some of the fluid flow is diverted from the flow used to drive the turbine and is used to create a hydrostatic bearings in both the axial and radial directions. One advantage of this design is the absence or minimization of any moving mechanical parts. In the embodiment illustrated in FIG. 14, device 300 includes housing or stator 302 and rotor 350 along with inlets 303 and outlet 307, stator passages 304 and stator outlets 305, turbine blades 355 and fluid channels 360 and ports 361 for supplying fluid to bearings 362 and 364.

In the various embodiments set forth herein, fabrication using one of the multi-layer, multi-material methods requires that special attention be given to the location of release holes or the like so that removal of sacrificial material (i.e. one of the multiple materials) can be readily achieved. This is particularly true in the case of the small channel sizes associated with the use of hydrostatic or hydrodynamic fluid bearings. In some alternative embodiments devices may be formed with larger gaps that are made smaller by shifting of components, and potentially locking components in place, after release of sacrificial material In still other alternative embodiments, holes may be made larger and then sealing techniques such as those set forth in U.S. patent application Ser. No. 10/434,103 may be used. This patent application is incorporated herein by reference as if set forth in full herein.

In some alternative embodiments, instead of the interior of the device forming the rotor and the exterior forming the stator these roles may be reversed as will be discussed hereinafter with regard to FIGS. 18A-18D.

In some alternative embodiments, the fluid may be pneumatic instead of hydraulic (e.g. air, nitrogen, argon, or the like instead of water, saline, or the like). Such alternatives may even use combustible materials along with a combustion source to increase pressure and thus increased velocity or torque achievable by the device. Such devices may present issues for medical applications but may be well suited for non-medical applications.

The device of the first embodiment, was fabricated and successfully tested using compressed air. As fabricated the turbine used 300 um diameter ball bearings and the overall diameter of the device was 1200 um. Of course with smaller bearings, smaller diameter and shorter devices could be fabricated.

Figure 15A:
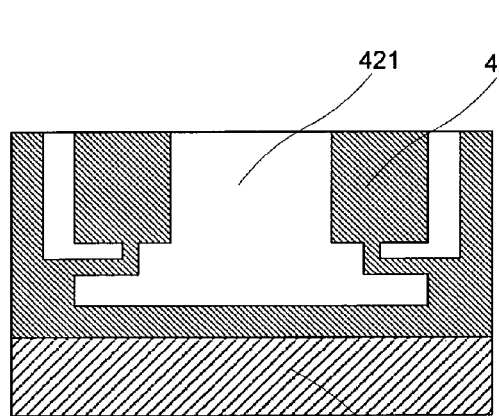
FIGS. 15A-15H illustrate various states in a method of embedding balls during fabrication of a turbine according to a fourth embodiment of the invention.
Figure 15B:
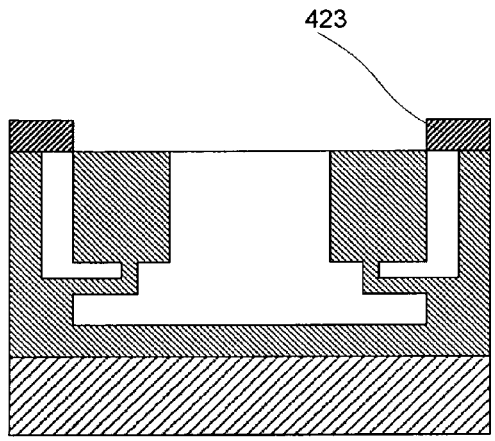
Figure 15C:
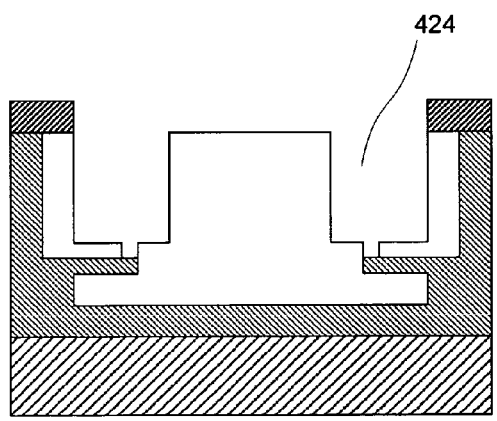
Figure 15D:
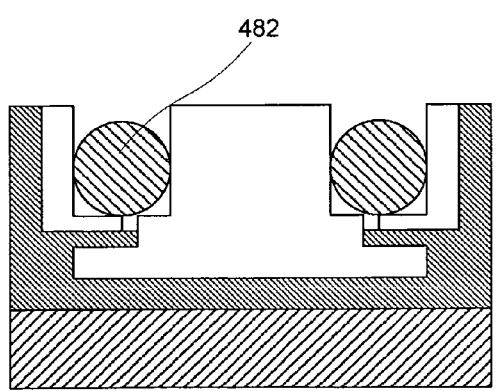
Figure 15E:
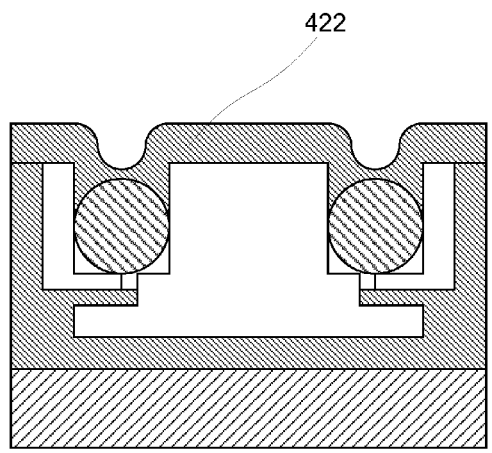
Figure 15F:
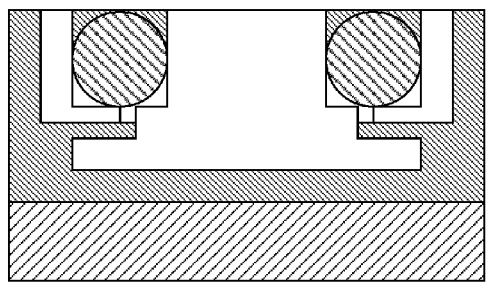
Figure 15G:
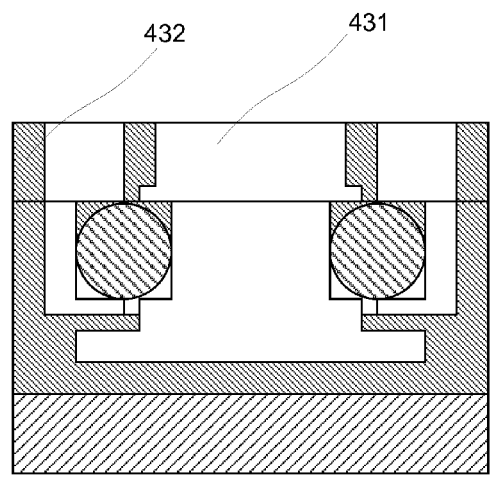
Figure 15H:
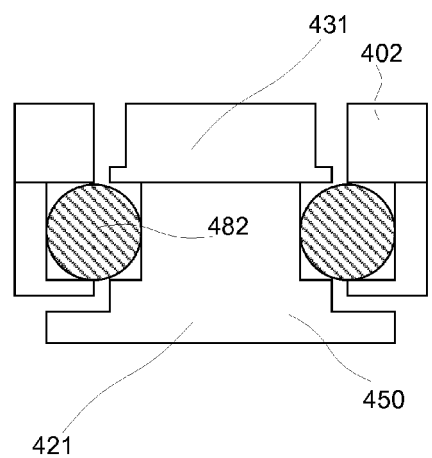

FIGS. 15A-15H illustrate various states in a method of embedding balls 482 during fabrication of a turbine according to a fourth embodiment of the invention (the turbine is built upside-down as shown, though it doesn't have to be). In this design the inner and outside races are fabricated with vertical walls, at least from their mid-points up since curved walls would prevent inserting the balls from above. FIG. 15A shows the state of the process after formation of a plurality of multi-material layers has occurred such that structural material 421 and sacrificial material 422 have been deposited to form a portion of a rotor and stator. FIG. 15B depicts the state of the process after deposition and patterning of a mask material (e.g. photoresist) so as to block those portions of sacrificial material not located between stator bearing and rotor bearing surfaces. FIG. 15C shows the state of the process after sacrificial material has been removed to create gaps 424 between rotor bearing and stator bearing surfaces (i.e. between the bearing races) while FIG. 15D shows the state of the process after loading bearings 482. An important part of the process is that the holes that the bearing are loaded into are deep enough to allow continued formation of multi-material layers along with planarization operations. FIG. 15E shows the state of the process after depositing additional sacrificial material while FIG. 15F shows the state of the process after planarization of the structural material and newly deposited sacrificial material. FIG. 15G shows the state of the process after formation of a number of additional layers, of sacrificial material 432 and structural material 431 which may be different form sacrificial material 422 and structural material 421, so as to complete the multi-layer multi-material build up process. FIG. 15H shows the state of the process after etching away sacrificial material leaving behind the turbine including rotor 450 and stator 402 formed of structural materials 421 and 431 and loaded with ball bearings 482. The main elements of this process are: (1) form a partially completed device from a plurality of adhered layers, (2) remove sacrificial material from portions of one or more layers and insert bearings, (3) continue formation of additional layers to complete formation of the device, and (4) release the device including embedded bearings from sacrificial material.

Figures 1, 16A:
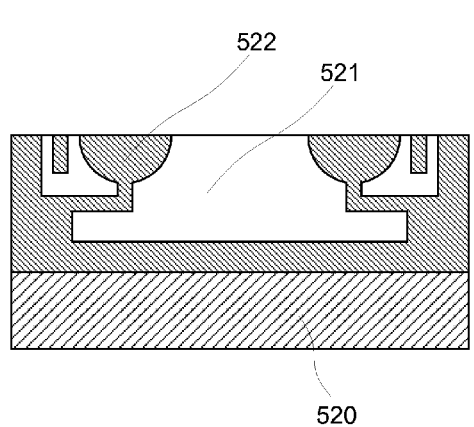
Figures 2, 16A:
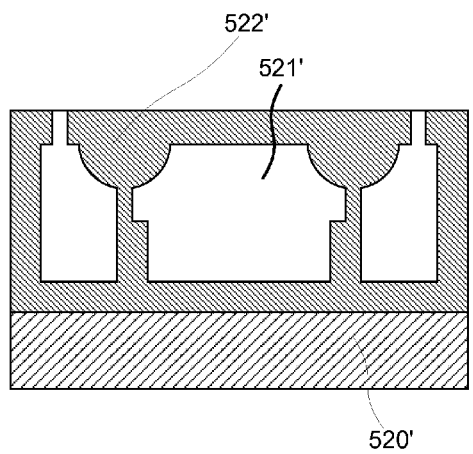
Figures 1, 16B:
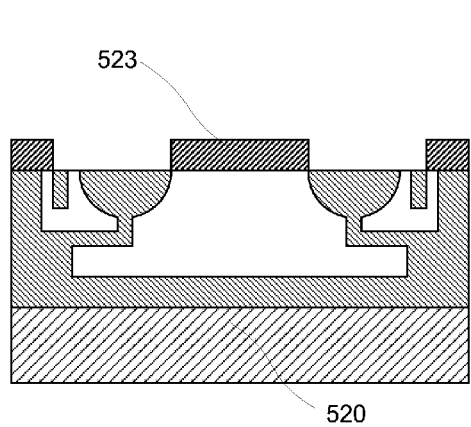
Figures 2, 16B:
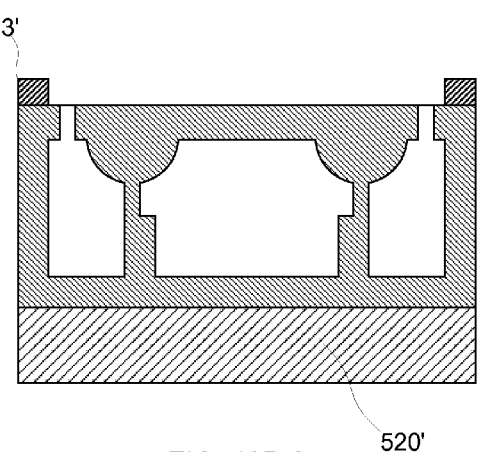
Figures 1, 16C:
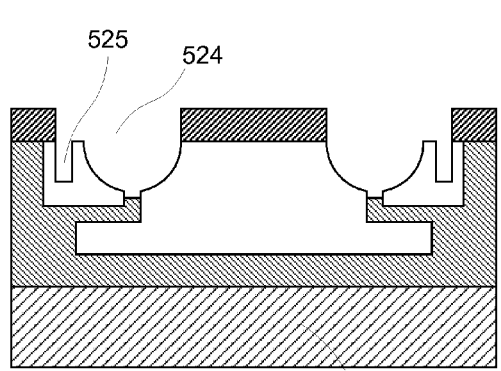
Figures 2, 16C:
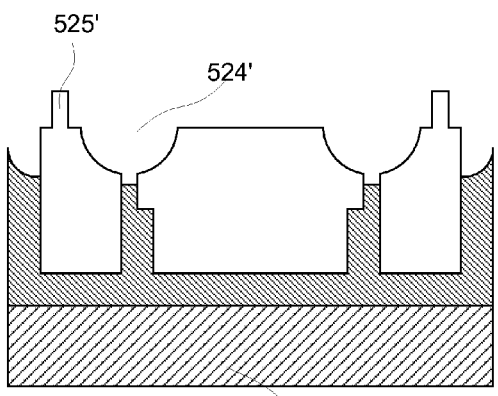
Figures 1, 16D:
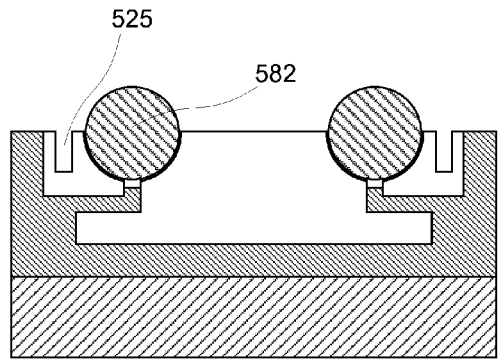
Figures 2, 16D:
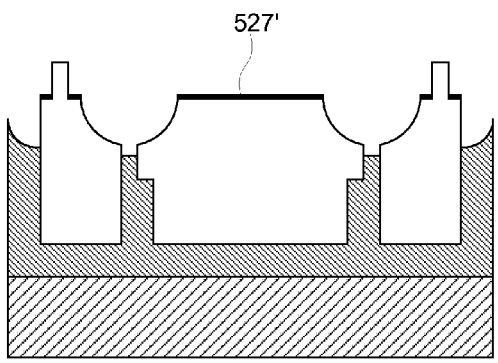
Figure 16E:
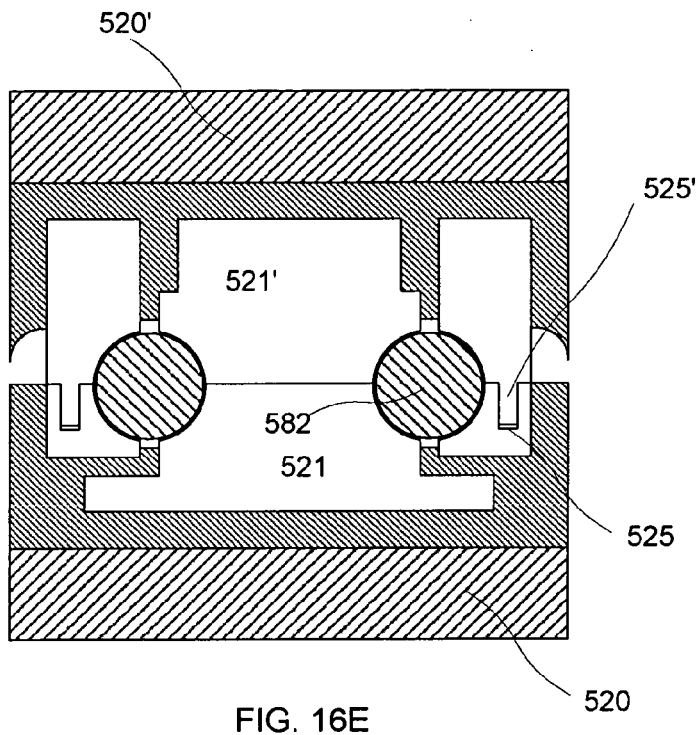
Figure 16F:
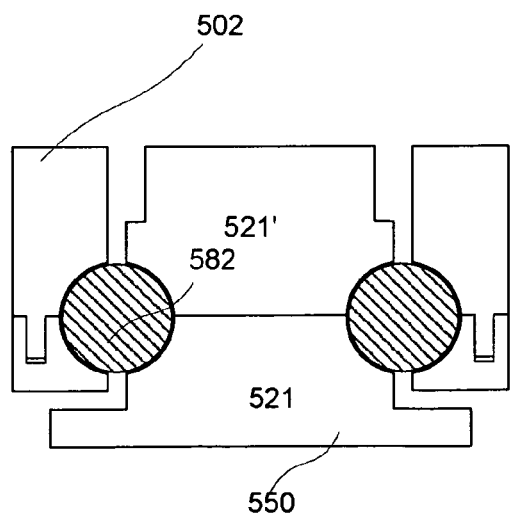

Of course numerous variations of this embodiment and process are possible. For example, bearings may be loaded at multiple levels after multiple intermediate etching operations have occurred. Other types of bearings may be incorporated. Multiple structural materials or sacrificial materials may be used during the formation of any particular layer FIGS. 16A-1 to 16F illustrate various states in a method of embedding balls during fabrication of a turbine according to a fifth embodiment of the invention. FIGS. 16A-1 and 16A-2 show and initial state of the process where a device has been partially formed in two halves one of which is upside down relative to the other. The left side shows the lower half of the device while the right side shows the upper half. According this embodiment, the device is formed using a multi-material, multi-component electrochemical fabrication process such that the two half elements are formed of a sacrificial material 522 and 522' and a structural material 521 and 521'. FIGS. 16B-1 and 16B-2 show the state of the process for the two half structures after depositing and patterning a masking material 523 and 523' (e.g. a photoresist) so as to allow selective removal of sacrificial material from portions of the half structures (e.g. from portions where ball bearings will need to be inserted). FIGS. 16C-1 and 16C-2 show the state of the process after removal of the sacrificial material to create gaps 524 and 524' in ball bearing placement locations, gaps 525 in alignment feature holes and protrusions 525' which will eventually be fitted into gaps 525. FIGS. 16D-1 and 16D-2 show the state of the process after bearings 582 have been loaded and adhesive 527' has been located on selective mating surfaces in the half structure of FIGS. 16D-2. FIG. 16E shows the state of the process after the right half has been flipped over and placed on the left half (e.g. via alignment elements 525 and 525') and the two halves bonded via adhesive 527'. FIG. 6F shows the state of the process after the device including rotor 550, stator 502, and bearing 582 have been released from substrates 520 and 520' and from the sacrificial material(s).

As with the previous embodiment, numerous variations of the process of FIGS. 16A-16F are possible and will be apparent to one of skill in the art upon review of the teachings set forth herein.

Figure 17A:
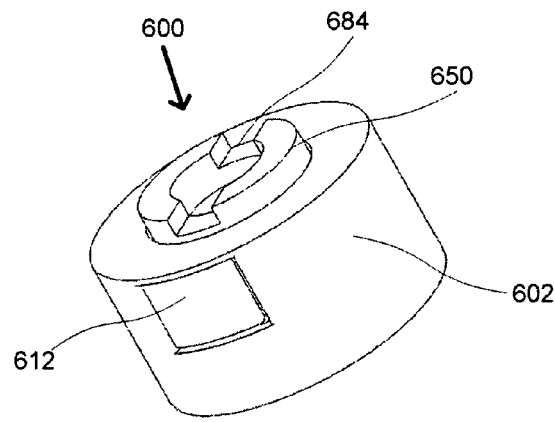

FIGS. 17A and 7B provide top and bottom perspective views of a turbine 600 similar to that of the embodiment of FIGS. 5-11 with the exception that the cutting tool is replaced by a coupling element 684 that can accept different tools. The device includes housing or stator 602 along with inlet holes 603 and outlet 607, bearing hole plug 612, rotor 650 holding blades 655. FIG. 17C provides a cut perspective view of the turbine of FIGS. 17A and 17B prior to the loading of ball bearing into the bearing races.

Figure 17B:
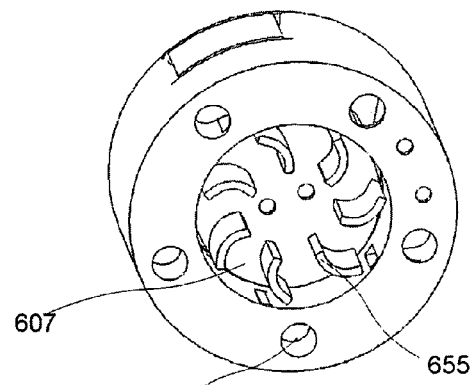
Figure 17C:
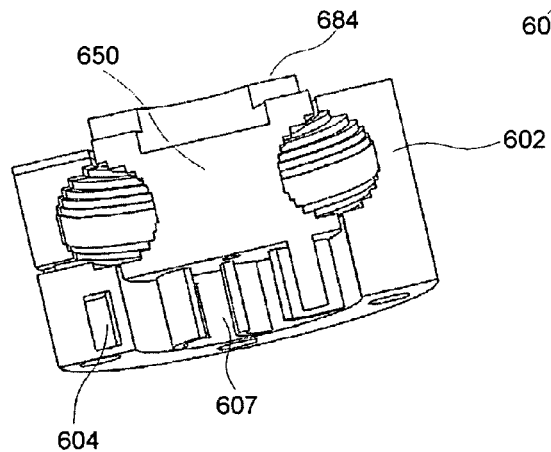
Figure 18A:
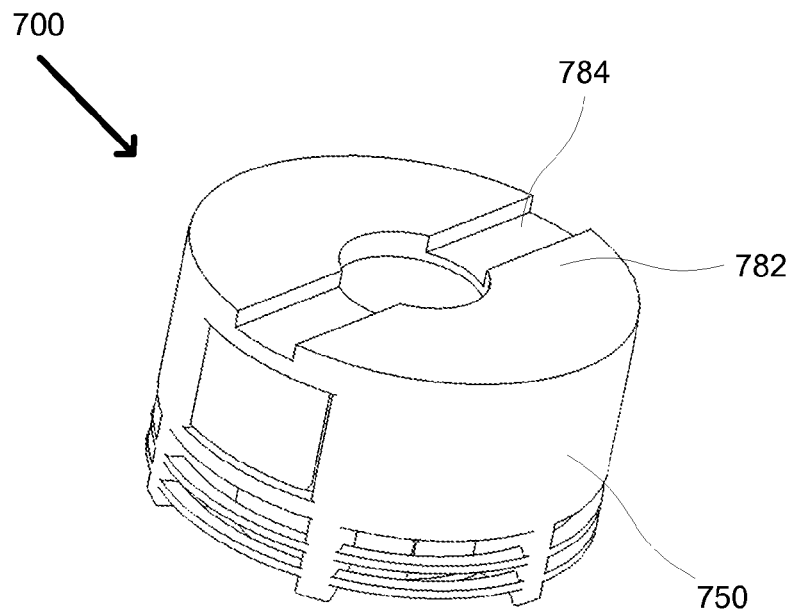
FIGS. 18A and 18B provide top and bottom perspective views of a turbine according to a seventh embodiment of the invention which is similar to that of FIGS. 17A and 17B with the exception that instead of being configured to take inlet fluid from the outside (larger radius) and directing it radially inward, the device is configured to take inlet fluid from the central portion of the axis of the device and to direct it radially outward (i.e. toward regions radially further from the axis of the device while FIG. 18C provides a perspective cut view of the device of FIGS. 18A and 18B and FIG. 18D provide a perspective cut view through the fluid flow channels of the stator.
Figure 18B:
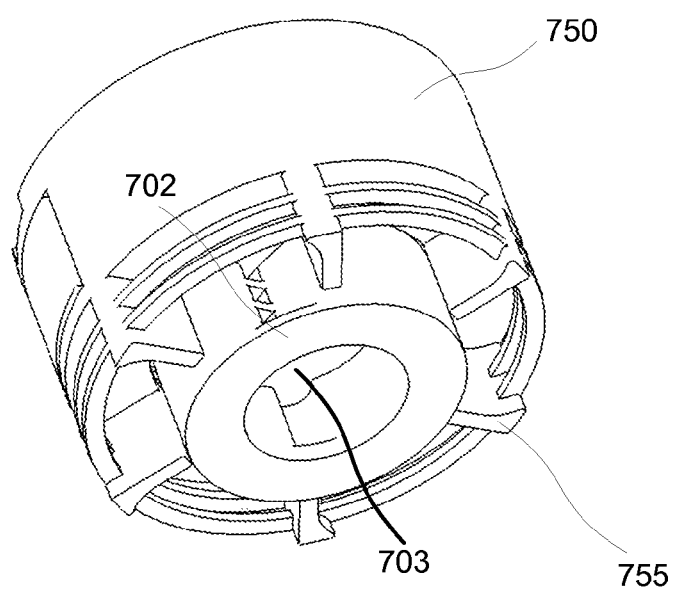
Figure 18C:
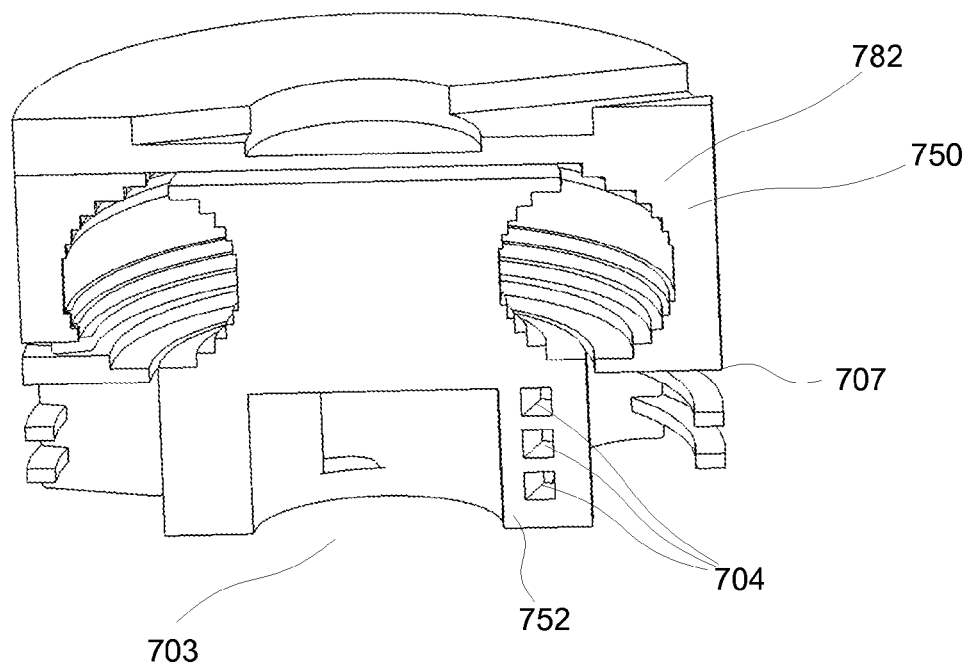
Figure 18D:
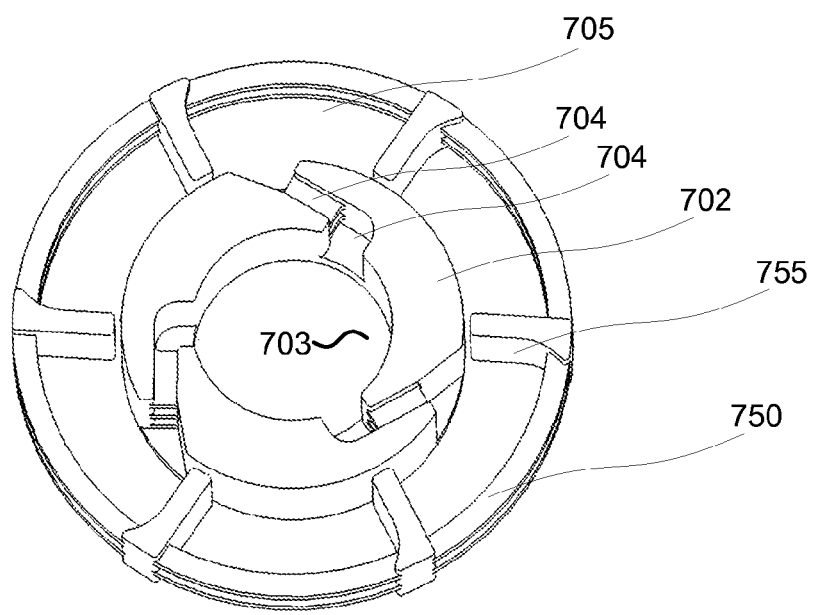

FIGS. 18A and 18B provide top and bottom perspective views of a turbine 700 similar to that of FIGS. 17A and 17B with the exception that instead of being configured to take inlet fluid from the outside (larger radius) and directing it radially inward, the device is configured to take inlet fluid from the central portion of the axis of the device 703 and directing it through passages 704 radially outward toward blades 755 (i.e. toward regions radially further from the axis of the device). FIG. 18C provides a perspective cut view of the device of FIGS. 18A and 18B while FIG. 18D provides a sectional view of the a portion of the rotor 750 and of the stator 702 so that passage 704 connecting inlet 703 with outlet 705 can be seen.

FIGS. 19A-19D provides various views of a blender tool, as an example of a tool, that is capable of being used with the turbines of FIGS. 17A-17C. The blender is configured so that housing 802 is mounted to a stator of a turbine like that of FIGS. 17A-17C wherein rotor 850 can be made to spin when driven by a turbine or the like. Housing 802 includes inlet 803 and outlet 807 while the rotor includes conical steps 876 which directs blended material outward through outlets 807. Rotor includes upper blades 872 having downward slopping surfaces 874 for pulling material deeper into the blender blades 855.

Figure 19A:
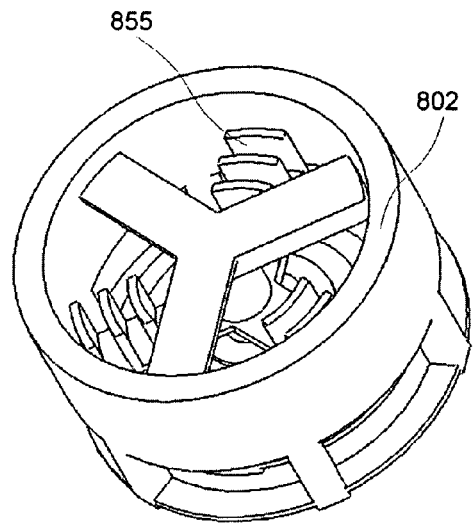
FIGS. 19A-19D provide various views of a blender tool, as an example of a tool according to an eighth embodiment of the invention, that is capable of being used with the turbine of FIGS. 17A-17C.
Figure 19B:
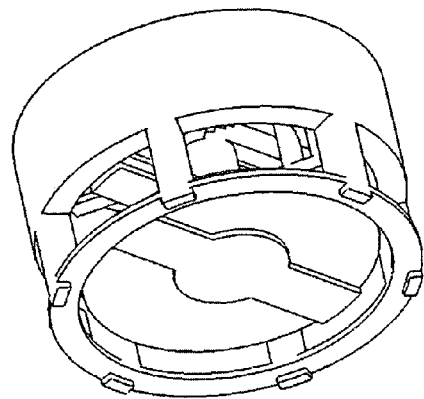
Figure 19C:
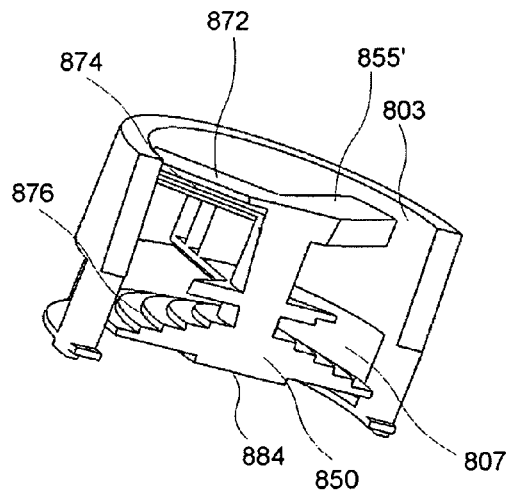
Figure 19D:
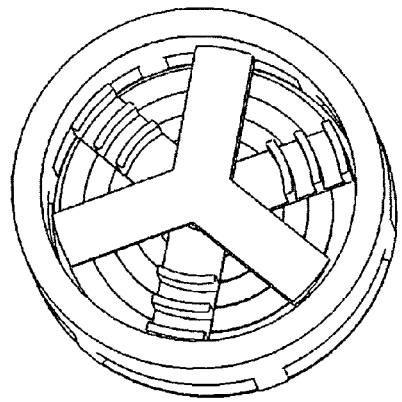
Figure 19E:
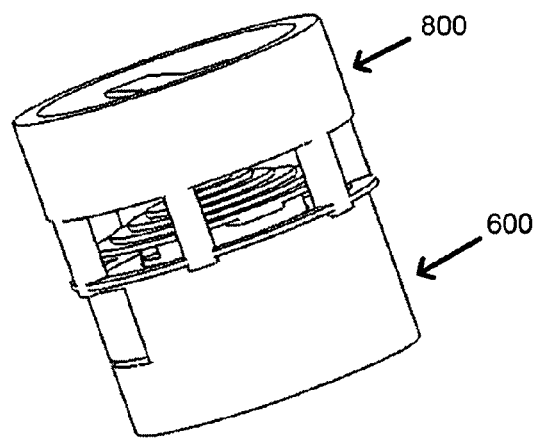
FIGS. 19E-19G provide various view of the blender of FIGS. 19A-19D along with the turbine of FIGS. 17A-17C.
Figure 19F:
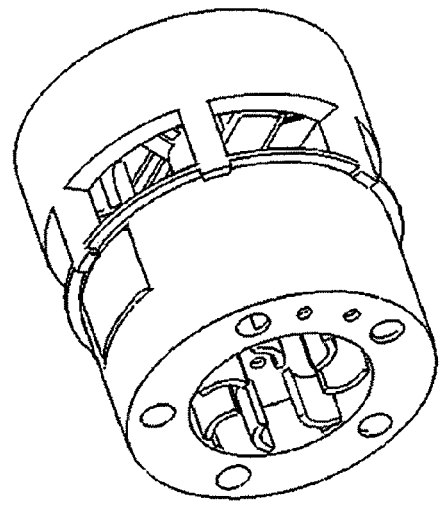
Figure 19G:
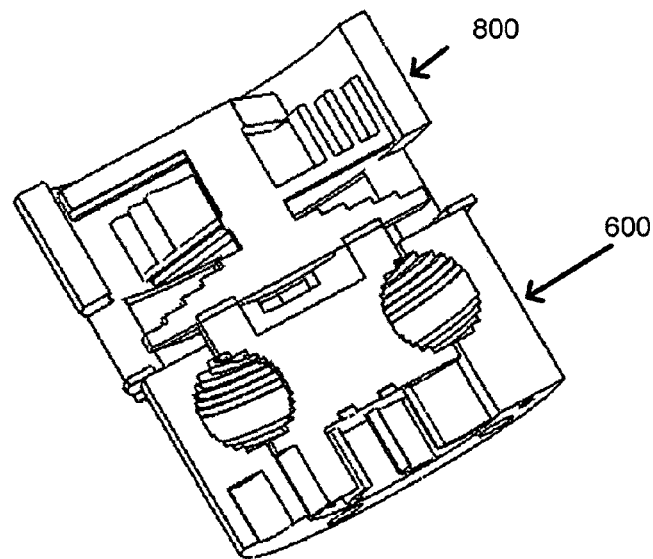

FIGS. 19E-19F provide various views of the blender device 800 of the eighth embodiment of the invention along with a turbine 600 of the sixth embodiment of the invention.

The bearings and races and bearing-race loading methods discussed herein may be used in non-turbine applications, such as (1) micro-motors and rotary actuators, (2) linear (e.g., recirculating ball) stages, (3) stabilization of the axes of IVUS and OCT catheters during rotation (to obtain a more accurate imaging), and (4) to reduce friction between drive cables and catheters for various devices that are driven using a proximal source of power.

In some variations of the embodiments presented above of the turbine devices, or similar structures, may serve as a centrifugal-type pumps. Such pumps can be driven by a motor, by a rotating drive cable, or by a turbine (e.g., one liquid can be used to pump another, without mixing).

In some variations of the embodiments presented above, gearing, etc. may be provided (e.g., co-fabricated with the turbine) to reduce or increase speed or torque.

In some variations of the embodiments presented above, the turbines may be used to produce a variable, near-static torque if the rotor is equipped with magnets and produces Eddy currents in a nearby conducting disk (or alternatively, the disk can be spun by the turbine rotor): as speed increases, so will torque.

Further Comments and Conclusions

The devices of the present application can be combined with various features of the devices taught in a number of additional patent applications, filed by Microfabrica, related to medical devices, to derive new and improved embodiments. These applications include: U.S. patent application Ser. No. 12/134,188, filed Jun. 5, 2008, directed to micro umbrella devices, expansion devices and chain mail devices for use in medical applications; U.S. patent application Ser. No. 12/138,404, filed Jun. 12, 2008, directed to coil delivery devices for use in medical applications; U.S. patent application Ser. No. 12/138,395, filed Jun. 12, 2008, directed to biopsy devices; U.S. patent application Ser. No. 12/138,336, filed Jun. 12, 2008, directed to micro-scale ratcheting devices for use in medical applications; 12/139,445, filed Jun. 13, 2008, directed to hydraulic and pneumatic devices; and 12/140,243, filed Jun. 16, 2008, directed to microreamers. Each of these applications is incorporated herein by reference as if set forth in full herein.

Structural or sacrificial dielectric materials may be incorporated into embodiments of the present invention in a variety of different ways. Such materials may form a third material or higher deposited material on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384 which was filed May 7, 2004 by Cohen et al. which is entitled "Method of Electrochemically Fabricating Multilayer Structures Having Improved Interlayer Adhesion" and which is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. patent application Ser. No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, entitled Methods of and Apparatus for Electrochemically Fabricating Structures Via Interlaced Layers or Via Selective Etching and Filling of Voids. The techniques disclosed in this referenced application may be combined with the techniques and alternatives set forth explicitly herein to derive additional alternative embodiments. In particular, the structural features are still defined on a planar-layer-by-planar-layer basis but material associated with some layers is formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full.

The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| U.S. patent application Ser. No., Filing Date US App Pub No, Pub Date | Inventor, Title |
|---|---|
| 09/493,496 - Jan. 28, 2000 | Cohen, "Method For Electrochemical Fabrication" |
| 10/677,556 - Oct. 1, 2003 | Cohen, "Monolithic Structures Including Alignment and/or Retention Fixtures for Accepting Components" |
| 10/830,262 - Apr. 21, 2004 | Cohen, "Methods of Reducing Interlayer Discontinuities in Electrochemically Fabricated Three-Dimensional Structures" |
| 10/697,597 - Dec. 20, 2002 | Lockard, "EFAB Methods and Apparatus Including Spray Metal or Powder Coating Processes" |
| 10/841,100 - May 7, 2004 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-0221668A - Dec. 4, 2003 | Cohen, "Electrochemical Fabrication Method and Application for Producing Three-Dimensional Structures Having Improved Surface Finish" |
| 10/434,294 - May 7, 2003 2004-0065550A - Apr. 8, 2004 | Zhang, "Electrochemical Fabrication Methods With Enhanced Post Deposition Processing" |
| 10/434,315 - May 7, 2003 2003-0234179 A - Dec. 25, 2003 | Bang, "Methods of and Apparatus for Molding Structures Using Sacrificial Metal Patterns" |
| 10/434,103 - May 7, 2004 2004-0020782A - Feb. 5, 2004 | Cohen, "Electrochemically Fabricated Hermetically Sealed Microstructures and Methods of and Apparatus for Producing Such Structures" |
| 10/841,006 - May 7, 2004 | Thompson, "Electrochemically Fabricated Structures Having Dielectric or Active Bases and Methods of and Apparatus for Producing Such Structures" |
| 10/841,347 - May 7, 2004 | Cohen, "Multi-step Release Method for Electrochemically Fabricated Structures" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733,195 - Apr. 9, 2007 | Kumar, "Methods of Forming Three-Dimensional Structures Having Reduced Stress and/or Curvature" |
| 11/506,586 - Aug. 8, 2006 | Cohen, "Mesoscale and Microscale Device Fabrication Methods Using Split Structures and Alignment Elements" |
| 10/949,744 - Sep. 24, 2004 | Lockard, "Three-Dimensional Structures Having Feature Sizes Smaller Than a Minimum Feature Size and Methods for Fabricating" |

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A device capable of converting a flow of a fluid into rotational mechanical motion, comprising:
   a. a stator;
   b. a rotor capable of rotational motion relative to the stator, wherein the rotational motion occurs about a rotational axis;
   c. a plurality of bearing elements positioned between the rotor and stator to hold the rotor and the stator in desired relative positions;
   d. an inlet in said stator for receiving a fluid and an outlet in said stator for removing fluid;
   wherein at least a portion of the stator and the rotor are formed using a multi-layer, multi-material electrochemical fabrication process, and
   wherein at least one bearing element is located within a slot in the rotor and a slot in the stator.

2. The device of claim 1 wherein the slot in the rotor faces radially outward and the slot in the stator faces radially inward.

3. The device of claim wherein the slot in the rotor faces radially inward and the slot in the stator faces radially outward.

4. The device of claim 1 wherein the slot in the rotor faces axially upward and the slot in the stator faces radially downward.

5. The device of claim 4 wherein at least two rotor slots and at least two stator slots exist wherein the two rotor slots face in opposite directions and the two stator slots face in opposite directions.

6. A method for fabricating a rotary device, comprising:
   a. forming at least a portion of a stator and a rotor from a plurality of adhered layers of material wherein the stator comprises a stator bearing surface, wherein the rotor comprises a rotor bearing surface, and wherein the forming of each layer of material comprises,
      i. depositing at least a first material;
      ii. depositing at least a second material; and
      iii. planarizing the first and second materials to a common level;
   b. removing at least a portion of the first or second material after formation of the plurality of layers;
   c. supplying a plurality of bearing elements;
   d. inserting the bearing elements into an opening between the stator bearing surface and the rotor bearing surface.

7. The method of claim 6 wherein bearing elements are inserted after formation of the stator and rotor are completed.

8. The method of claim 6 additionally comprising:
   a. forming at least one additional layer to complete formation of the stator and the rotor after inserting the bearing elements, wherein the forming of the at least one additional layer comprises:
      i. depositing at least a first material;
      ii. depositing at least a second material; and
      iii. planarizing the first and second materials to a common level; and
   b. removing least a portion of the first or second material after formation of the at least one additional layer.

9. The method of claim 6 wherein the stator and the rotor are formed in substantially assembled positions relative to each other.

10. The method of claim 6 wherein the stator and the rotor are formed separately from one another and are thereafter inserted into assembled positions and bearing elements are inserted.

11. The method of claim 6 wherein the forming of the plurality of adhered layers comprises forming lower portions of the stator and rotor in assembled positions forming upper portions of the stator and rotor in assembled positions but laterally spaced from the lower portions and upside down relative to the lower portions and wherein the method additionally comprises removing sacrificial material from inside a gap region on the lower portions intended to receive bearing elements and a gap region on the upper portions intended to receiving bearing elements, applying bearing elements into at least one of the gap region in the lower portion or in the upper portion and then bring a mating surface of the lower portion and a mating surface of the upper portion into desired relative positions and affixing the lower portions and upper portions together.

12. The method of claim 11 wherein the affixing occurs via a bonding material.

13. The method of claim 11 wherein the affixing occurs via one or more catches formed along with one or both of the lower portion and the upper portion.

14. A method for fabricating a rotary device, comprising:
   a. forming at least a portion of a stator, a rotor, and a plurality of bearing elements from a plurality of adhered layers of material wherein the stator comprises a stator bearing surface including a plurality of protrusions separated by indentations, wherein the rotor comprises a rotor bearing surface including a plurality of protrusions separated by indentations, and wherein the bearing elements comprise an outer surface including a plurality of protrusions separated by indentations, and wherein the forming of each layer of material comprises:
      i. depositing at least a first material;
      ii. depositing at least a second material; and
      iii. planarizing the first and second materials to a common level;
   b. removing least a portion of the first or second material after formation of the plurality of layers; and
   c. supplying a plurality of bearing elements, and
   wherein during formation, at least some protrusions on the stator bearing surface and on the rotor bearing surface align with indentations on the outer surface of the bearing elements and wherein at least some indentations on the rotor bearing surface and on the stator bearing surface align with protrusions on the outer surface of the bearing elements, such that gaps between the bearing elements and the rotor and stator surfaces on any given layer are larger than a minimum feature size but wherein on at least some adjacent layers, gaps are substantially less than the minimum feature size.

* * * * *